US006103890A

United States Patent [19]
Jarvis et al.

[11] Patent Number: 6,103,890
[45] Date of Patent: Aug. 15, 2000

[54] ENZYMATIC NUCLEIC ACIDS THAT CLEAVE C-FOS

[75] Inventors: Thale Jarvis; James A. McSwiggen, both of Boulder; Dan T. Stinchcomb, Ft. Collins, all of Colo.

[73] Assignee: Ribozyme Pharmaceuticals, Inc., Boulder, Colo.

[21] Appl. No.: 08/998,099

[22] Filed: Dec. 24, 1997

Related U.S. Application Data

[63] Continuation-in-part of application No. 08/373,124, Jan. 13, 1995, Pat. No. 5,646,042, which is a continuation-in-part of application No. 08/245,466, May 18, 1994, abandoned
[60] Provisional application No. 60/037,658, Jan. 23, 1997.
[51] Int. Cl.$^7$ ............................ C07H 21/04; C12P 19/34; C12N 15/63; C12N 15/85
[52] U.S. Cl. .................. 536/24.5; 435/91.31; 435/320.1; 435/325; 435/375
[58] Field of Search .......................... 435/6, 69.1, 91.31, 435/440, 325, 352, 366, 375, 320.1; 530/23.1, 23.5, 24.3, 24.31, 24.33, 24.5; 514/44

[56] References Cited

U.S. PATENT DOCUMENTS

| | | | |
|---|---|---|---|
| 4,987,071 | 1/1991 | Cech et al. | 435/91.31 |
| 5,168,053 | 12/1992 | Altman | 514/44 |
| 5,213,580 | 5/1993 | Slepian et al. | 623/1 |
| 5,328,470 | 7/1994 | Nabel et al. | 604/101 |
| 5,334,711 | 8/1994 | Sproat et al. | 536/24.5 |
| 5,525,468 | 6/1996 | McSwiggen | 435/6 |

FOREIGN PATENT DOCUMENTS

| | | |
|---|---|---|
| 0 360 257 A2 | 3/1990 | European Pat. Off. . |
| 91/03162 | 3/1991 | WIPO . |
| 91/15580 | 10/1991 | WIPO . |
| 91/18624 | 12/1991 | WIPO . |
| 92/07065 | 4/1992 | WIPO . |
| 93/15187 | 8/1993 | WIPO . |
| 93/23057 | 11/1993 | WIPO . |
| 93/23569 | 11/1993 | WIPO . |
| 94/02595 | 2/1994 | WIPO . |
| 95/04818 | 2/1995 | WIPO . |
| 96/08558 | 3/1996 | WIPO . |
| 96/22689 | 8/1996 | WIPO . |
| 97/10334 | 3/1997 | WIPO . |
| 97/18312 | 5/1997 | WIPO . |

OTHER PUBLICATIONS

Gura, T. Science. vol. 278, pp. 1041–1042 ( Nov. 1997).
Crooke , S.T. in Antisense Research and Application ( Stanley T. Crooke, Ed), Springer–Verlag, pp. 1–50, (Jul. 1998).
Branch, A.D. TIBS. vol. 23, pp. 45–50 (Feb. 1998).
Gewirtz, A.M. et al. Proc. Natl. Acad. Sci. USA. vol. 93, pp. 3161–3163 ( Apr. 1996).
Rojanasakul, Y. Advanced Drug Delivery Reviews. vol. 18, pp. 115–131 (Jan. 1996).
Anderson, W.F. Nature. vol. 392, Suppl. pp. 25–30 (Apr. 1998).

Aktar et al., "Cellular Uptake and Intracellular Fate of AntiSense Oligonucleotides, " *Trends Cell Biol.* 2:139–144 (1992).
Alitalo et al., "Aberrant Expression of An Amplified c–myb Oncogene in Two Cell Lines From a Colon Carcinoma," *Proc. Natl. Acad. Sci. USA* 81:4534–4538 (1984).
Anfossi et al., "An Olitomer Complementary to c–myb–encoded Mrna Inhibits Proliferation of Human Myeloid Leukemia Cell Lines," *Proc. Natl. Acad. Sci. USA* 86:3379–3383 (1979).
Angel et al., "The Role of Jun, Fos and the AP–1 Complex in Cell–Proliferation and Transformation," *Biochimica et Biophysica Acta* 1072:129–157 (1991).
Austin et al., "Intimal Proliferation of Smooth Muscle Cells as an Explanation for Recurrent Coronary Artery Stenosis After Percutaneous Transluminal Coronary Angioplasty," *JACC* 6(2):369–75 (1985).
Belaaouaj et al., "Human Macrophage Metalloelastase," *J. Biol. Chem.* 270(24):14568–14575 (1995).
Bennett et al., "Cationic Lipids Enhance Cellular Uptake and Activity of Phosphorothioate Antisense Oliogonucleotides," *Mol. Pharmacol.* 41:1023–1033 (1991).
Burgin et al., "Chemically Modified Hammerhead Ribozymes with Improved Catalytic Rates," *Biochem.* 35:14090–14097 (1996).
Carter, "Adeno–associated Virus Vectors," *Curr. Opi. Biotech.* 3:533 (1992).
Cech, "Ribozymes and Their Medical Implications," *JAMA* 260:3030 (1988).
Chen et al., "Multitarget–ribozyme Directed to Cleave at up to Nine Highly Conserved HIV–1 Env RNA Regions Inhibits HIV–1 Replication—Potential Effectiveness Against Most Presently Sequenced HIV–1 Isolates," *Nucl. Acid Res.* 20(17):4581–4589 (1992).
Chowrira et al., "Extensive Phosphorothioate Substitution Yields Highly Active and Nuclease–resistant Hairpin Ribozymes," *Nucl. Acids Res.*20(11):2835–2840 (1992).
Chowrira et al., "In Vitro and In Vivo Comparison of Hammerhead, Hairpin and Hepatitis Delta Virus Self–processing Ribozyme Cassettes," *J. of Biol. Chem.* 269(41):25856–25864 (1994).
Christofferson et al., "Ribozymes as Human Therapeutic Agents," *Am. Chem. Soc.*38(12):2023–2037 (1995).
Christofferson et al., "Application of Computational Technologies to Ribozyme Biotechnology Products, " *J. Mol. Struc. Theochem.* 311:273 (1994).
Collins and Olive, "Reactions Conditions and Kinetics of Self–Cleavage of a Ribozyme Derived from Neurospora VS RNA, " *Biochemistry* 32:2795–2799 (1993).
Contrino et al., In Situ Detection of Tissue Factor in Vascular Endothelial Cells: Correlation with the Malignant Phenotype of Human Breast Disease, *Nature Med.*2:209 (1996).
Couture et al., "Anti–Gene Therapy: Use of Ribozymes to Inhibit Gene Function," *TIG*12(12):510 (1996).

(List continued on next page.)

*Primary Examiner*—John S. Brusca
*Assistant Examiner*—Mark L. Shibuya
*Attorney, Agent, or Firm*—Lyon & Lyon LLP

[57] ABSTRACT

Enzymatic nucleic acid molecules which cleave c-fos RNA.

19 Claims, 10 Drawing Sheets

OTHER PUBLICATIONS

Dreyfus, "Restriction Ribozymes?" *Einstein J. of Biol. And Med.*6(2):92–93 (1988).

Dropulic et al., "Functional Characterization of a U5 Ribozyme: Intracellular Suppression of Human Immunodeficiency Virus type 1 Expression," *J.of Virol.* 66(3):1432–1441 (1992).

Elroy–Stein et al., "Cytoplasmic Expression System Based on Constitutive Synthesis of Bacteriophage T7RNA Polymerase in Mammalian Cells," *Proc. Natl. Acad. Sci. USA* 87:6743–6747 (1990).

Feldstein et al., "Two Sequences Participating in the Autolytic Processing of Satellite Tobacco Ringspot Virus Complementary RNA, " *Gene* 82:53–61 (1989).

Felts et al., "Tissue Factor Gene Transcription in Serum–Stimulated Fibroblasts Is Mediated by Recruitment of c–Fos into Specific AP–1 DNA–Binding Complexes," *Biochemistry* 34:12355 (1995).

Forster et al., "External Guide Sequences for an RNA Enzyme," *Science* 249:783–786 (1990).

Ritchlin and Winchester, "Potential Mechanisms for Coordinate Gene Activation in the Rheumatoid Synoviocyte: Implications and Hypotheses," *Springer Semin. Immunopathol.* 11:219 (1989).

Rochefort, "Oestrogen–and Anti–Oestrogen–Regulated Genes in Human Breast Cancer," *Oestrogens and Breast Cancer* 254–268 (1995).

Rossi et al., "Ribozymes as Anti–HIV–1 Therapeutic Agents: Principles, Applicationsm and Problems" *Aids Res. And Human Retro.* 8(2):183–189 (1992).

Ruther et al.,"*c–fos* Expression Induces Bone Tumors in Transgenic Mice," *Oncogene* 4:861–865 (1989).

Saarialho–Kere et al., "Distinct Localization of Collagenase and Tissue Inhibitor of Metalloproteinases Expression in Wound Healing Associated with Ulcerative Pyogenic Granuloma," *J. Clin. Invest.* 90:1952–1957 (1992).

Sarver et al., "Ribozymes as Potential Anti–HIV–1 Therapeutic Agents," *Science* 247:1222–1225 (1990).

Sato et al., "Regulatory Mechanism of 92kDa Type IV Collagenase Gene Expression Which is Associated with Invasiveness of Tumor Cells," *Oncogene* 8:395–405 (1993).

Saville and Collins, "A Site–Specific Self–Clevage Products of a Neurospora Mitochondrial Plasmid Transcript," *Proc. Natl. Acad. Sci.* 88:8826–8830 (1991).

Scanlon et al., "Ribozyme–Mediated Reversal of the Multidrug–Resistant Phenotype," *Proc. Natl. Acad. Sci. USA* 91:11123 (1994).

Scanlon et al., "Ribozyme–Mediated Cleavage of C–fos mRNA Reduces Gene Expression of DNA Synthesis Enzymes and Metallothionein," *Proc. Natl. Acad. Sci. USA* 88: 10591–10595 (1991).

Scaringe et al., "Chemical Synthesis of Biologically Active Oligoribonucleotides Using β–cyanoethyl Protected Ribonucleoside Phosphoramidites," *Nucl.Acids Res.*18(18):5433–5441 (1990).

Taira et al., "Construction of a Novel RNA–Transcript–Trimming Plasmid Which can be Used both In Vitro in Place of Run–off and (G)–free Transcriptions and In Vivo as Multi–Sequences Transcription Vectors, " *Nucl. Acids Res.* 19(19):5125–5130 (1991).

Thompson et al., "Improved Accumulation and Activity of Ribozymes Expressed from a tRNA–based RNA Polymerase III Promoter," *Nucl. Acids Res.* 23(12):2259–2268 (1995).

Troen et al., "Downstream Sequences Mediate Induction of the Mouse Carhepsin L Promoter by Phorbol Ester," *Cell Growth & Diff.* 2:23–31 (1991).

Uhlenbeck, "A Small Catalytic Oligoribonucleotide, " *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an Escherichia Coli Formylmethionine tRNA," *Am. Chem. Soc.* 109:7845–7854 (1987).

Usman et al., "Chapter 30. Catalytic RNA (Ribozymes) as Drugs," *Annual Reports in Medicinal Chem.* 30: 285–294 (1995).

Lauricella–Lefebvre et al., "Stimulation of the 92–kD Type IV Collagenase Promoter and Enzyme Expression in Human Melanoma Cells," *Invasion Metastasis* 13:289–300 (1993).

Lengyel et al., "Stimulation of Urokinase Expression by TNF–αRequires the Activation of Binding Sites for the AP–1 and PEA3 Transcription Factors," *Elsevier* 1268:65–72 (1995).

Li et al., "Cleavage by Rnase P of Gene N mRNA Reduces Bacteriophage λBurst Size, " *Nucl. Acids Res.* 24(5):835–842 (1996).

Lieber et al., "Stable High–Level Gene Expression in Mammalian Cells by T7 Phage RNA Polymerase," *Methods Enzymol.* 217:47–66 (1993).

Lin et al., "Inhibition of Collagenase Type I Expression by Psoralen Antisense Oligonucleotides in Dermal Fibroblasts," *The FASEB J.* 9:1371–1377 (1995).

Lisziewicz et al., "Inhibition of Human Immunodificiency Virus Type 1 Replication by Regulated Expression of a Polymeric Tat Activation Response RNA Decoy as a Strategy for Gene Therapy in AIDS," *Proc. Natl. Acad. Sci.USA* 90:8000–8004 (1993).

MacDougall et al., "Contributions of Tumor and Stromal Matrix Metalloproteinases to Tumor Progression, Invasion and Metastasis," *Cancer and Metastasis Rev.* 14:351–362 (1995).

McGarry et al., "Inhibition of Heat Shock Protein Synthesis by Heat–inducible Antisense RNA, " *Proc. Natl. Acad. Sci. USA* 83:399–403 (1986).

Michaels et al., "Conversion of a Group II Intron into a New Multiple–Turnover Ribozyme That Selectively Cleaves Oligonrcleotides: Elucidation of Reaction Mechanism and Structure/Function Relationships," *Biochem.* 34:2965–2977 (1995).

Milligan et al., "Synthesis of Small RNAs Using T7 RNA Polymerase," *Methods in Enzymol.*180:51–62 (1989).

Morgan et al., "Stimulus–Transciption Coupling in the Nervous System: Involvement of the Inducible Proto–Onocogenes *fos* AND *jun*," *Annu. Rev. Neurosci.* 14:421–451 (1991).

Ohkawa et al., "Activiteis of HIV–RNA Targeted Ribozymes Transcribed from a 'Shot–gun'Type Ribozymes–trimming Plasmid," *Oxford Unv. Press* 27:15–16 (1992).

Ojwang et al., "Inhibition of Human Immunodeficiency Virus Type 1 Expression by a Hairpin Ribozyme, " *Proc. Natl. Acad. Sci. USA* 89:10802–10806 (1992).

Okada et al., "Localization of Matrix Metalloproteinase 3 (Stromelysin) in Osteoarthritic Cartilage and Synovium," *Lab Inv.* 66(6):680–690 (1992).

Perrault et al., "Mixed Deoxyribo–and Ribo–Oligonucleotides with Catalytic Activity," *Nature* 344:565 (1990).

Perrotta et al., "Clevage of Oliogoribonucleotides by a Ribozyme Derived from the Hepatitis ♀Virus RNA Sequence," *Am. Chem. Soc.* 31:16–21 (1992).

Pieken et al., "Kinetic Characterization of Ribonuclease–Resistant 2'–Modified Hammerhead Ribozymes," *Science* 253:314–317 (1991).

Ransone et al., "Nuclear Proto–Oncogenes Fos and Jun, " *Annu. Rev.Cell Biol.* 6:539–557 (1990).

Rijnders et al., "Expression of Cellular Oncogenes in Human Prostateic Carcinoma Cell Lines," *Biochem and Biophys. Res. Comm.* 132(2):548–554 (1985).

Funato et al., "The Utility of an Anti*fos* Ribozyme in Reversing Cisplatin Resistance in Human Carcinomas," *Advan. Enzyme Regul.* 32:195–209 (1992).

Gaire et al., "Structure and Expression of the Human Gene for the Matrix Metalloproteinase Matrilysin," *J. of Biol. Chem.* 269(3):2032–2040 (1994).

Gao et al., "Cytoplasmic Expression of a Reporter Gene by Co–Delivery of T7 RNA Polymerase and T7 Promoter Sequence with Cationic Liposomes," *Nucl. Acids Res.* 21(12):2867–2872 (1993).

Griffin Jr. et al., "Group II Intron Ribozymes that Cleave DNA and RNA Linkages with Similar Efficiency, and Lack Contacts with Substrate 2'–hydroxyl Groups," *Chem. & Biol.* 2(11):761–770 (1995).

Guerrier–Takada et al.,"The RNA Moiety of Ribonuclease P Is the Catalytic Subunit of the Enzyme," *Cell*35:849–857 (1983).

Guo et al., "Efficient Trans–cleavage of a Stem–loop RNA Substrate by a Ribozyme Derived from Neurospora VS RNA," *Embo J.* 14(2):368–376 (1995).

Hadman et al., "Isolation and Cloning of JTAP–1: A Cathepsin Like Gene Upregulated in Response to V–Jun Induced Cell Transformation," *Oncogene* 12:135–142 (1996).

Hampel et al., "'Hairpin' Catalytic RNA Model: Evidence for Helices and Sequence Requirement for Substrate RNA," *Nucl. Acid Res.* 18(2):299–304 (1990).

Hampel et al., "RNA Catalytic Properties of the (–)s TRSV Sequence," *Biochem.* 28:4929–4933 (1989).

Haseloff et al., "Simple RNA Enzymes With New and Highly Specific Endoribonuclease Activities," *Nature* 334:585–591 (1988).

Haseloff et al., "Sequences Required for Self–Catalysed Clevage of the Satellite RNA of Tobacco Ringspot Virus," *Gene* 82:43–52 (1993).

Hembry et al., "Immunolocalisation Studies on Six Matrix Metalloproteinases and their Inhibitors, TIMP–1 and TIMP–2, in Synovia from Patients with Osteo–and Rheumatoid Arthritis, " *Ann. Rheum. Dis.* 54:25–32 (1995).

Hertel et al., "Numbering System for the Hammerhead," *Nucl. Acids Res.* 20(12):3252 (1992).

Izant et al., "Constitutie and Conditional Suppression of Exongenous and Endogenous Genes by Anti–Sense RNA, " *Science* 229:345—3552 (1985).

Jaeger et al., "Improve Predictions of Secondary Structures for RNA," *Proc. Natl. Acad. Sci. USA* 86:7706–7710 (1989).

Jeffries et al., A "Catalytic 13–mer Ribozyme, " *Nucl. Acid Res.* 17(4): 1371–1377 (1989).

Kashani–Sabet et al., "Reversal of the Malignant Phenotype by an Anti–ras Ribozyme," *Antisense Res. Dev.* 2:3–15 (1992).

Kim et al., "Three–dimensional Model of the Active Site of the Self–Splicing rRNA Precursor of Tetrahymena, " *Proc. Natl. Acad. USA* 84:8788–8792 (1987).

Kushtai et al., "The *c–fos* Proto–Oncogene inMurine 3LL Carcinoma Clones Controls the Expresiion of MHC Genes," *Oncogene* 2:119–127 (1988).

L'Hullier et al., "Cytoplasmic Delivery of Ribozymes Leads to Efficient Reduction in α–Lactalbumin mRNA Levels in C1271 Mouse Cells, " *EMBO J.* 11(12):4411–4418 (1992).

Usman et al., "Exploiting the Chemical Synthesis of RNA," *TIBS*17:334–339 (1992).

Van Straaten et al., "Complete Nucleotide Sequence of a Human *c–onc* gene: Deduced Amino Acid Sequence of the Human *c–fos* Protein," *Proc. Natl. Acad. Sci. USA* 80:3183–3187 (1983).

Ventura et al., "Activation of HIV–Specific Ribozymes Activity by Self–Clevage," *Nucl. Acids Res.* 21(14):3249–3255 (1993).

Wang et al., "A Novel Target Cell for C–*fos*–Induced Oncogenesis: Developement of Chondrogenic Tumours in Embryonic Stem Cell Chimeras," *EMBO J.* 10(9):2437–2450 (1991).

Wargnier et al., "Identification of Human Granzyme B Promoter Regulatory Elements Interacting with Activated T–Cell–Specific Proteins: Implication of Ikaros and CBF Binding Sites in Promoter Activation,"*Proc. Natl. Acad. Sci. USA* 92:6930–6934 (1995).

Weerasinghe et al., "Resistance to Human Immunodeficiency Virus Type 1 (HIV–1) Infection in Human CD4[+] Lymphocyte–Derived Cell Lines Conferred by Using Retroviral Vectors Expressing an HIV–1 RNA–Specific Ribozyme, " *J. of Virol.* 65(10):5531–5534 (1991).

Wincott et al., "Synthesis, Deprotection, Analysis and Purification of RNA and Ribozymes," *Nucl. Acids Res.* 23(14):2677–2684 (1995).

Wu et al., "The Proto–Oncogene *c–fos* is over–expressed in the Majority of Human Osteosarcomas," *Oncogene* 5:989–1000 (1990).

Yu et al., "A Hairpin Ribozyme Inhinits Expression of Diverse Strains of Human Immunodeficiency Virus Type 1, " *Proc. Natl. Acad. Sci* 90:6340–6344 (1993).

Zabner et al., "Adeovirus–Mediated Gene Transfer Transiently Corrects the Chloride Transport Defect in Nasal Epithelia of Patients with Cystic Fibrosis, " *Cell* 75:207–216 (1993).

Zaug et al., "The Tetrahymena Ribozyme Acts Like an RNA Restriction Endonuclease, " *Nature* 324:429–433 (1986).

Zhou et al., "Synthesis of Functional mRNA in Mammalian Cells by Bacteriophage T3 RNA Polymerase," *Mol. and Cell. Biol* 10(9):4529–4537 (1990).

ENZYMATIC NUCLEIC ACIDS THAT CLEAVE C-FOS

CROSS-REFERENCE TO RELATED APPLICATIONS

This application claims the benefit of Thale Jarvis et al., U.S. Provisional Application, U.S. Ser. No. 60/037,658, entitled "Enzymatic Nucleic Acid Treatment of Diseases or Conditions Related to Levels of C-fos," filed Jan. 23, 1997, and is a continuation-in-part of Stinchcomb et al., "Methods and Compositions for the Treatment of Restenosis and Cancer using Ribozymes," U.S. Ser. No. 08/373,124, filed Jan. 13, 1995, and now U.S. Pat. No. 5,646,042, which is a continuation-in-part of Stinchcomb et al., "Methods and Compositions for the Treatment of Restenosis and Cancer Using Ribozymes," U.S. Ser. No. 08/245,466, and filed May 18, 1994, now abandoned. All of these are hereby incorporated by reference herein in their totality including any drawings and figures.

BACKGROUND OF THE INVENTION

The present invention concerns therapeutic compositions and methods for the treatment of cancer.

The present invention relates to therapeutic compositions and methods for the treatment or diagnosis of diseases or conditions related to c-fos expression levels, such as cancer. The discussion is not meant to be complete and is provided only for understanding of the invention that follows. This summary is not an admission that any of the work described below is prior art to the claimed invention.

The c-fos proto-oncogene encodes a transcription factor that plays an important regulatory role in the response to mitogenic stimuli (for a review see Angel et al., 1991, *Biochem. Biophys. Acta*. 1072, 129). Evidence in the literature indicates that c-fos is necessary for expression of many matrix metallo-proteinases (MMPs), including stromelysin 1, stromelysin 2, collagenase 1, matrylisin, 92 kD gelatinase and human macrophage metalloelastase (Sato et al., 1993, *Oncogene* 8, 395; Gaire et al. 1994 *J Biol Chem* 269, 2032; Lauricell-Lefebvre et al. 1993 *Invasion Metastasis* 13, 289; Belaaouajet al. 1995 *J Biol Chem* 270, 14568). C-fos also regulates the expression of other proteases including urokinase-type plasminogen activator, granzyme B and several cathepsins (Lengyel et al., 1995 *Biochim Biophys Acta* 1268, 65; Troen et al., 1991 *Cell Growth Differ* 2, 23; Hadman et al., 1996 *Oncogene* 12, 135; Rochefort et al., 1995, *Ciba Found Symp* 191, 254; Wargnier et al. 1995 *Proc Natl Acad Sci, USA* 92, 6930). Applicant believes that the implications of several of these proteases in tumor metastasis indicates that inhibition of c-fos has the potential to reduce invasive phenotype, as claimed herein. In addition to regulating protease expression, c-fos is necessary for expression of tissue factors, which play an important role in angiogenesis (Felts et al., 1995, *Biochemistry* 34, 12355; Contrino et al., 1996, *Nature Med* 2, 209). C-fos is required for expression of the mdr-1 gene (multi-drug resistance), which is thought to contribute to failures in chemotherapy (Scanlon et al., 1994, *Proc Natl Acad Sci, USA* 91, 11123). C-fos has been shown to play a role in cell proliferation in some cell types (Rijnders et al., 1985, *Biochem Biophys Res Comm* 132, 548). There is also some suggestion that c-fos may have a role in neuronal injury, degeneration, cell death and/or neoplasms (Schlingensiepen et al., International PCT Publication No. WO 95/02051).

The proto-oncogene c-fos is the cellular homolog of the v-fos gene from FBJ murine osteosarcoma virus. Members of the Fos protein family (c-fos, fosB, fra-1 and fra-2) form heterodimers with members of the jun family (c-jun/AP-1, junB and junD). The heterodimers act as transcriptional activators by binding DNA at AP-1 sites present in a variety of genes, including collagenase, IL-2, adipocyte P2, human metallothionein IIA, transin, and the DNA repair enzymes thymidylate (dTMP) synthase, DNA polymerase $\beta$, and topoisomerase I. Expression of c-fos is normally tightly regulated at both the RNA and protein level. The kinetics of expression follow the classic pattern of an immediate early gene; mRNA levels peak at 30–45 minutes following mitogenic stimulation and thereafter decline rapidly. The c-fos gene contains an AT-rich mRNA destabilizing sequence in 3' non-coding region, giving the mRNA a half-life of about 12 minutes. The Fos protein has a relatively short half-life (under 2 hours) and negatively regulates transcription of the c-fos gene, contributing to rapid down-regulation (Morgan et al., 1991 *Annu Rev Neurosci*. 14, 421–451; Ransone et al., 1990, *Annu Rev Cell Biol* 6, 539).

The connection between fos expression and osteosarcoma was first suggested by the identification of v-fos in murine osteosarcoma virus. Greater than 90% of mice infected with the fos viruses FBJ-MSV and FBR-MSV develop bone tumors. It appears that deregulated expression of the normal c-fos gene can result in similar oncogenic transformation. For example, overexpression of c-fos in tissue culture cells yields a transformed phenotype, and in transgenic mice results in a high frequency of bone and cartilage tumors. The majority of human osteosarcomas (HOS) exhibit significantly elevated c-fos levels (Wu et al. 1990 *Oncogene* 5, 989). Unlike ras, no specific c-fos mutations have been identified that correlate with oncogenic potential.

Transgenic mice that constitutively express c-fos develop normally until a few weeks after birth, when bone hyperplasia becomes evident (Ruther et al., 1989 *Oncogene* 4, 861). Approximately 20% develop bone tumors. The level of c-fos expression is at least 10-fold higher in tumor tissue compared to normal tissue. Interestingly, although constitutive expression of c-fos occurs in many tissues, lesions are confined to bone tissue. Thus a secondary tissue-specific event is probably required in addition to elevated c-fos levels to bring about malignant transformation. Fos expression is also associated with cartilage tumor formation when the transgene is expressed during embryogenesis (Wang et al., 1991 *EMBO J* 10, 2437).

Homozygous c-fos knock-out mice are normal at birth, then begin to exhibit osteopetrosis at about 11 days. This is characterized by severe ossification of the marrow space, shortened bones, and absence of tooth eruption due to obstruction by abnormal amounts of bone. In addition, although possessing normal motor skills, the transgenic animals show behavioral abnormalities including hyperactivity and severely diminished response to external stimuli. This is consistent with reports showing that c-fos plays a pivotal role in the adaptive responses of the nervous system.

Normal bone is constantly being formed and resorbed by the tightly regulated action of osteoblasts and osteoclasts, respectively. This process is controlled in part by parathyroid hormone (PTH) which differentially affects bone mass depending on whether it is present continuously or intermittantly. PTH binds to receptors on osteoblasts and rapidly and transiently induces c-fos expression. PTH-activated osteoblasts then induce c-fos expression in osteoclasts and bone marrow stromal cells. Thus the temporally-regulated expression of c-fos may constitutute an essential downstream event in the normal response to PTH. Either deletion or constitutive overexpression of c-fos in transgenic mice produces abnormal bone morphology, illustrating the requirement for tightly regulated expression of this protein.

Scanlon, International PCT Publication Nos. WO 91/18624 and WO 96/08558; Scanlon et al., 1991, *Proc. Natl. Acad. Sci. USA.*, 88, 10591; and Funato et al., 1992, *Advan. Enzyme Regul.*, 32, 195, report the use of a hammerhead ribozyme to cleave a site within c-fos mRNA.

Scanlon, International PCT Publication No. WO 96/08558, states on page 9–10 that "[D]rug resistance in mammalian, including human, cancer cells is reversed or ameliorated by the downregulation of the expression of the Fos/Jun heterocomplex and of AP-responsive genes downstream from Fos/Jun in the transduction pathway. Reversal of MDR phenotype by ribozyme suppression of c-fos oncogene expression illustrates one practical application of the invention."

SUMMARY OF THE INVENTION

This invention relates to ribozymes, or enzymatic nucleic acid molecules, directed to cleave RNA species that are required for cellular growth responses. In particular, applicant describes the selection and function of ribozymes capable of cleaving RNA encoded by the oncogene, c-fos. Such ribozymes may be used to inhibit the hyperproliferation of tumor cells in one or more cancers.

In the present invention, ribozymes that cleave c-fos RNA are described. Moreover, applicant shows that these ribozymes are able to inhibit gene expression and cell proliferation in vitro and in vivo, and that the catalytic activity of the ribozymes is required for their inhibitory effect. From those of ordinary skill in the art, it is clear from the examples described, that other ribozymes that cleave target RNAs required for cell proliferation may be readily designed and are within the invention.

By "inhibit" is meant that the activity of c-fos or level of RNAs encoded by c-fos is reduced below that observed in the absence of the nucleic acid, particularly, inhibition with ribozymes preferably is below that level observed in the presence of an inactive RNA molecule able to bind to the same site on the mRNA, but unable to cleave that RNA.

By "enzymatic nucleic acid molecule" it is meant a nucleic acid molecule which has complementarity in a substrate binding region to a specified gene target, and also has an enzymatic activity which is active to specifically cleave RNA in that target. That is, the enzymatic nucleic acid molecule is able to intermolecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention.

The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme, oligozyme or DNA enzyme, as used in the art. All of these terminologies describe nucleic acid molecules with enzymatic activity.

By "equivalent" RNA to c-fos is meant to include those naturally occurring RNA molecules associated with cancer in various animals, including human, rat and pig.

By "complementarity" is meant a nucleic acid that can form hydrogen bond(s) with another RNA sequence by either traditional Watson-Crick or other non-traditional types (for example, Hoogsteen type) of base-paired interactions.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a ribozyme.

Nucleic acid molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, Einstein *Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371,1989).

Because of their sequence-specificity, trans-cleaving ribozymes show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the RNA nonfunctional and abrogates protein expression from that RNA. In this manner, synthesis of a protein associated with a disease state can be selectively inhibited.

Ribozymes that cleave the specified sites in c-fos RNAs represent a novel therapeutic approach to induce graft tolerance, treat autoimmune diseases, allergies, cancer and other inflammatory conditions. Applicant indicates that ribozymes are able to inhibit the activity of c-fos and that the catalytic activity of the ribozymes is required for their inhibitory effect. Those of ordinary skill in the art, will find that it is clear from the examples described that other ribozymes that cleave these sites in c-fos RNAs may be readily designed and are within the scope of this invention.

In one of the preferred embodiments of the inventions herein, the enzymatic nucleic acid molecule is formed in a hammerhead or hairpin motif, but may also be formed in the motif of a hepatitis δ virus, group I intron, group II intron or RNaseP RNA (in association with an RNA guide sequence) or Neurospora VS RNA. Examples of such hammerhead motifs are described by Dreyfus, supra, Rossi et a., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res.* 18, 299; of the hepatitis δ virus motif is described by Perrotta and Been, 1992 *Biochemistry* 31, 16; of the RNaseP motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; and of the Group I intron by Cech et al., U.S. Pat. No. 4,987,071. These specific motifs are not limiting in the invention and those skilled in the art will recognize that all that is important in an enzymatic nucleic acid molecule (or multiple fragments of such molecules) of this invention is that it has a specific substrate binding site or arm(s) which is complementary to one or more of the target gene RNA regions, and that it have nucleotide sequences within or surrounding that substrate binding site which impart an RNA cleaving activity to the molecule (enzymatic portion).

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding c-fos proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al., 1991, *Proc. Nati. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225; Thompson et al., 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT W093/23569, and Sullivan et al., PCT W094/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

Such ribozymes are useful for the prevention of the diseases and conditions discussed above, and any other diseases or conditions that are related to the levels of c-fos activity in a cell or tissue.

By "related" is meant that the inhibition of c-fos RNAs and thus reduction in the level respective protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables III and IV. Examples of such ribozymes are also shown in Tables III and IV. Examples of such ribozymes consist essentially of sequences defined in these Tables.

By "consists essentially of" is meant that the active ribozyme contains an enzymatic center or core equivalent to those in the examples, and binding arms able to bind mRNA such that cleavage at the target site occurs. Other sequences may be present which do not interfere with such cleavage.

Thus, in a first aspect, the invention features ribozymes that inhibit gene expression and/or cell proliferation. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target mRNAs, preventing translation and protein accumulation. In the absence of the expression of the target gene, cell proliferation is inhibited.

In a preferred embodiment, the enzymatic RNA molecules cleave c-fos mRNA and inhibit cell proliferation. Such ribozymes are useful for the prevention and/or treatment of cancer. Ribozymes are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. The ribozymes, similarly delivered, also are useful for inhibiting proliferation of certain cancers associated with elevated levels of the c-fos oncogene, particularly leukemias, neuroblastomas, and lung, colon, and breast carcinomas. Using the methods described herein, other enzymatic RNA molecules that cleave c-fos and thereby inhibit tumor cell proliferation may be derived and used as described above. Specific examples are provided below in the Tables and figures.

In another aspect of the invention, ribozymes that cleave target molecules and inhibit c-fos activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture and Stinchcomb, 1996, TIG., 12, 510).

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

By "vectors" is meant any nucleic acid- and/or viral-based technique used to deliver a desired nucleic acid.

These ribozymes, individually, or in combination or in conjunction with other drugs, can be used to treat diseases or conditions discussed above. For example, to treat a disease or condition associated with c-fos levels, the patient may be treated, or other appropriate cells may be treated, as is evident to those skilled in the art.

In a further embodiment, the described ribozymes can be used in combination with other known treatments to treat conditions or diseases discussed above. For example, the described ribozymes could be used in combination with one or more known therapeutic agents to treat cancer.

In preferred embodiments, the ribozymes have binding arms which are complementary to the sequences in the tables, shown as Seq. I.D. Nos. 1–140 and 325–368. Examples of such ribozymes are shown as Seq. I.D. Nos. 141–324. Other sequences may be present which do not interfere with such cleavage.

In another aspect of the invention, ribozymes that cleave target molecules and inhibit cell proliferation are expressed from transcription units inserted into DNA, RNA, or viral vectors. Preferably, the recombinant vectors capable of expressing the ribozymes are locally delivered as described above, and transiently persist in smooth muscle cells. Once expressed, the ribozymes cleave their target mRNAs and prevent proliferation of their host cells. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, Nature, 327, 596–600) into a substrate and enzyme portion; FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, Nucl. Acids. Res., 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "_____" refers to a covalent bond.

Figure 9A:
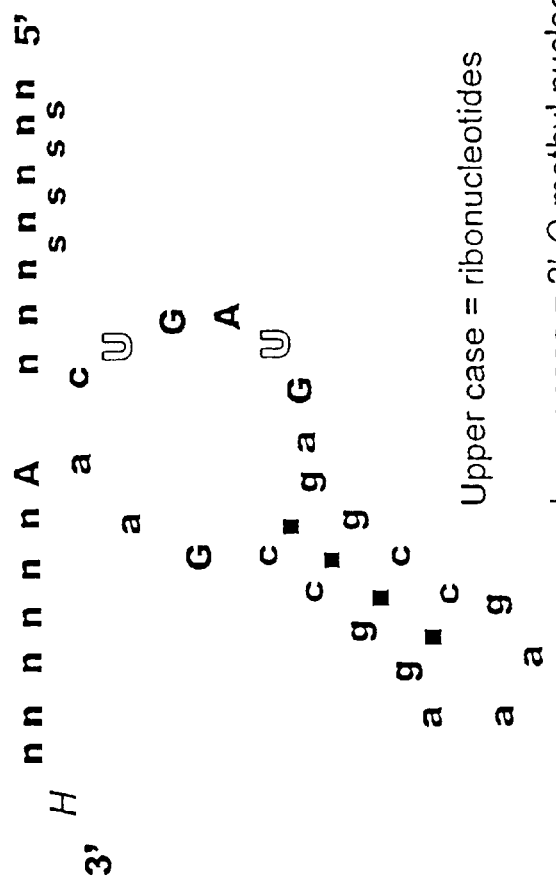
Figure 9B:
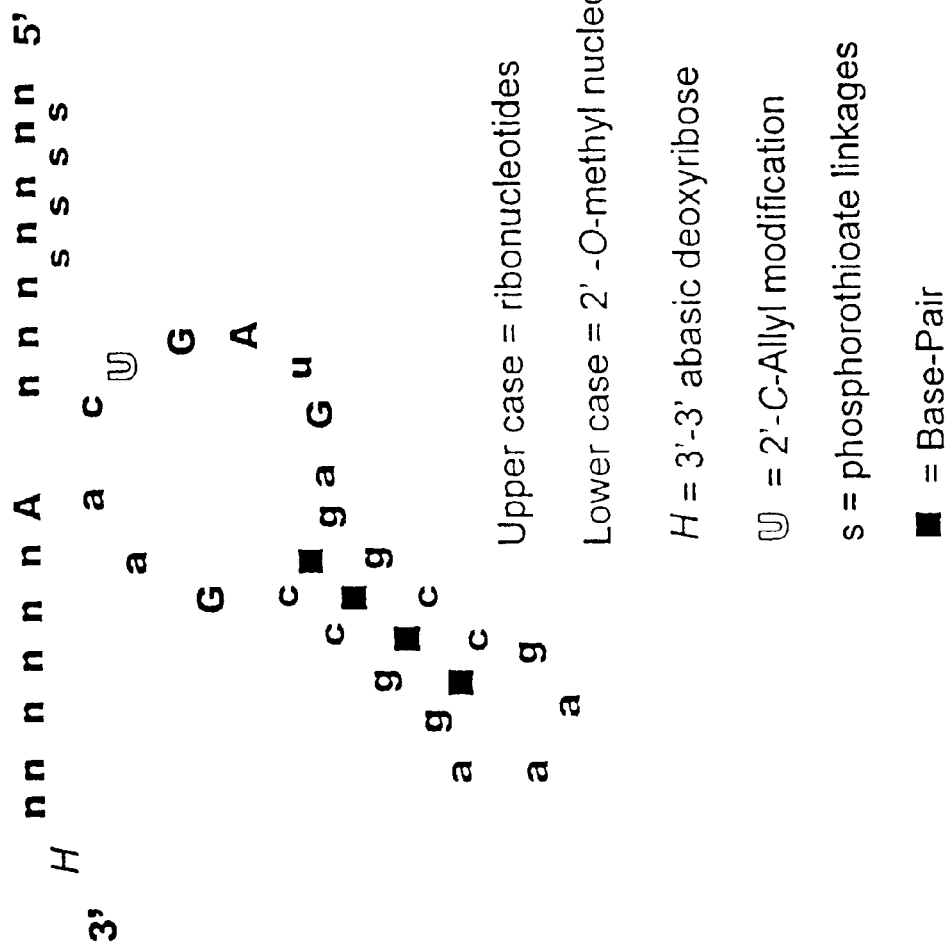

FIGS. 9A and 9B show generic structures of chemically modified hammerhead ribozymes. A) diagrammatic representation of Amino hammerhead ribozyme. B) diagrammatic representation of C-allyl hammerhead ribozyme.

TARGET SITES

Targets for useful ribozymes can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468 and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein.

The sequence of human c-fos mRNAs were screened for optimal ribozyme target sites using a computer folding algorithm. Hammerhead or hairpin ribozyme cleavage sites were identified. These sites are shown in Tables III and IV (All sequences are 5' to 3' in the tables) The nucleotide base position is noted in the Tables as that site to be cleaved by the designated type of ribozyme. The nucleotide base position is noted in the Tables as that site to be cleaved by the designated type of ribozyme.

Hammerhead or hairpin ribozymes were designed that could bind and were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684) and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:$H_2O$/3:1:1, vortexed and the supernatant was then added to the first supernatant. The combined supernatants, containing the oligoribonucleotide, were dried to a white powder.

The base-deprotected oligoribonucleotide was resuspended in anhydrous TEA•HF/NMP solution (250 μL of a solution of 1.5 mL N-methyl-pyrrolidinone, 750 μL TEA and 1.0 mL TEA•3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for $G_5$ and a U for $A_{14}$ (numbering from Hertel, K. J., et al., 1992, *Nucleic Acid Res.*, 20, 3252).

The average stepwise coupling yields were >98% (Wincott et al., 1995 *Nucleic Acids Res.* 23, 2677–2684).

Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51).

Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 6, 14090). Ribozymes are purified by gel electrophoresis using general methods or are purified by high pressure liquid chromatography (HPLC; See Wincott et al., supra) the totality of which is hereby incorporated herein by reference) and are resuspended in water.

The sequences of the ribozymes that are chemically synthesized, useful in this study, are shown in Tables III–IV. Those in the art will recognize that these sequences are representative only of many more such sequences where the enzymatic portion of the ribozyme (all but the binding arms) is altered to affect activity. For example, stem-loop II sequence of hammerhead ribozymes can be altered (substitution, deletion, and/or insertion) to contain any sequences provided a minimum of two base-paired stem structure can form. Similarly, stem-loop IV sequence of hairpin ribozymes listed in Tables IV (5'-CACGUUGUG-3') can be altered (substitution, deletion, and/or insertion) to contain any sequence, provided a minimum of two base-paired stem structure can form. Preferably, no more than 200 bases are inserted at these locations. The sequences listed in Tables II and IV may be formed of ribonucleotides or other nucleotides or non-nucleotides. Such ribozymes (which have enzymatic activity) are equivalent to the ribozymes described specifically in the Tables.

Optimizing Ribozyme Activity

Figure 1:
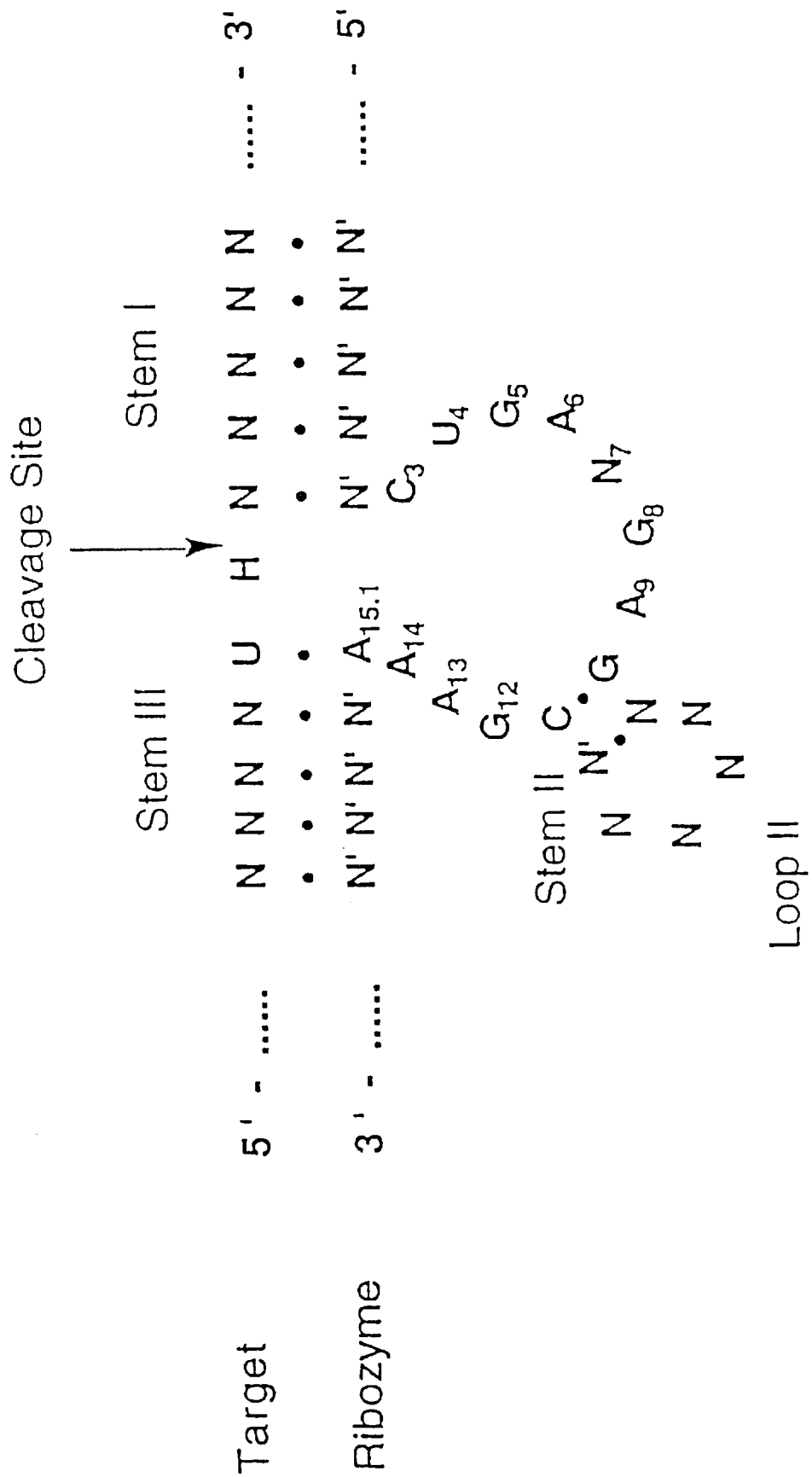
Figure 2A:
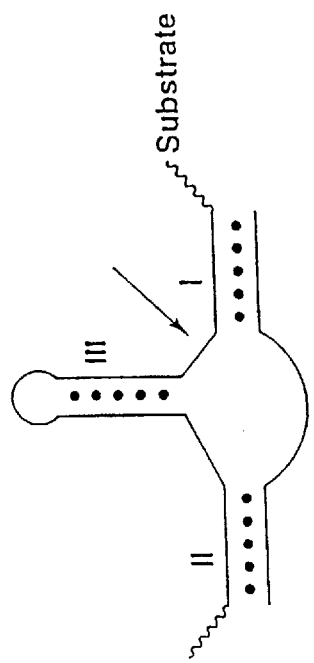
Figure 2B:
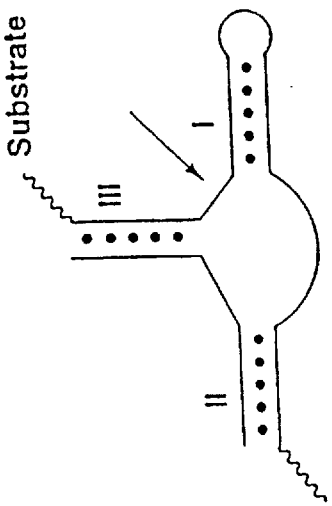
Figure 2C:
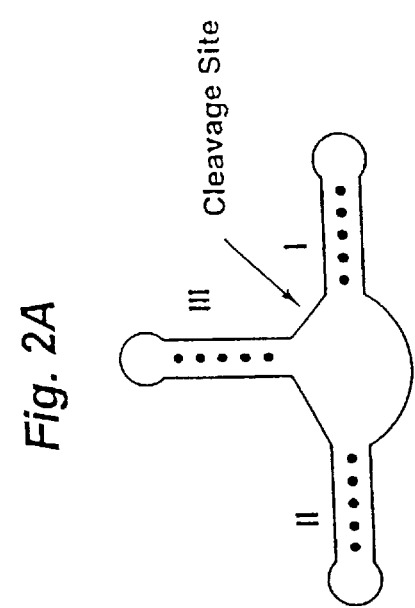
Figure 2D:
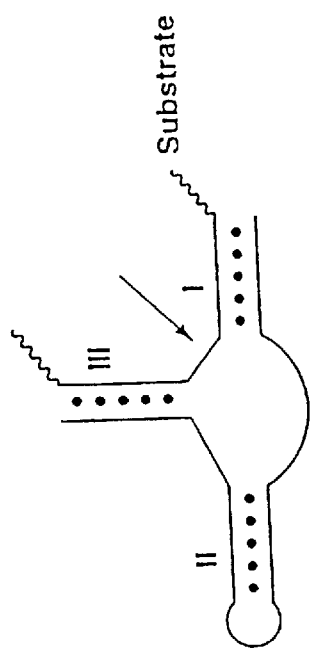
Figure 3:
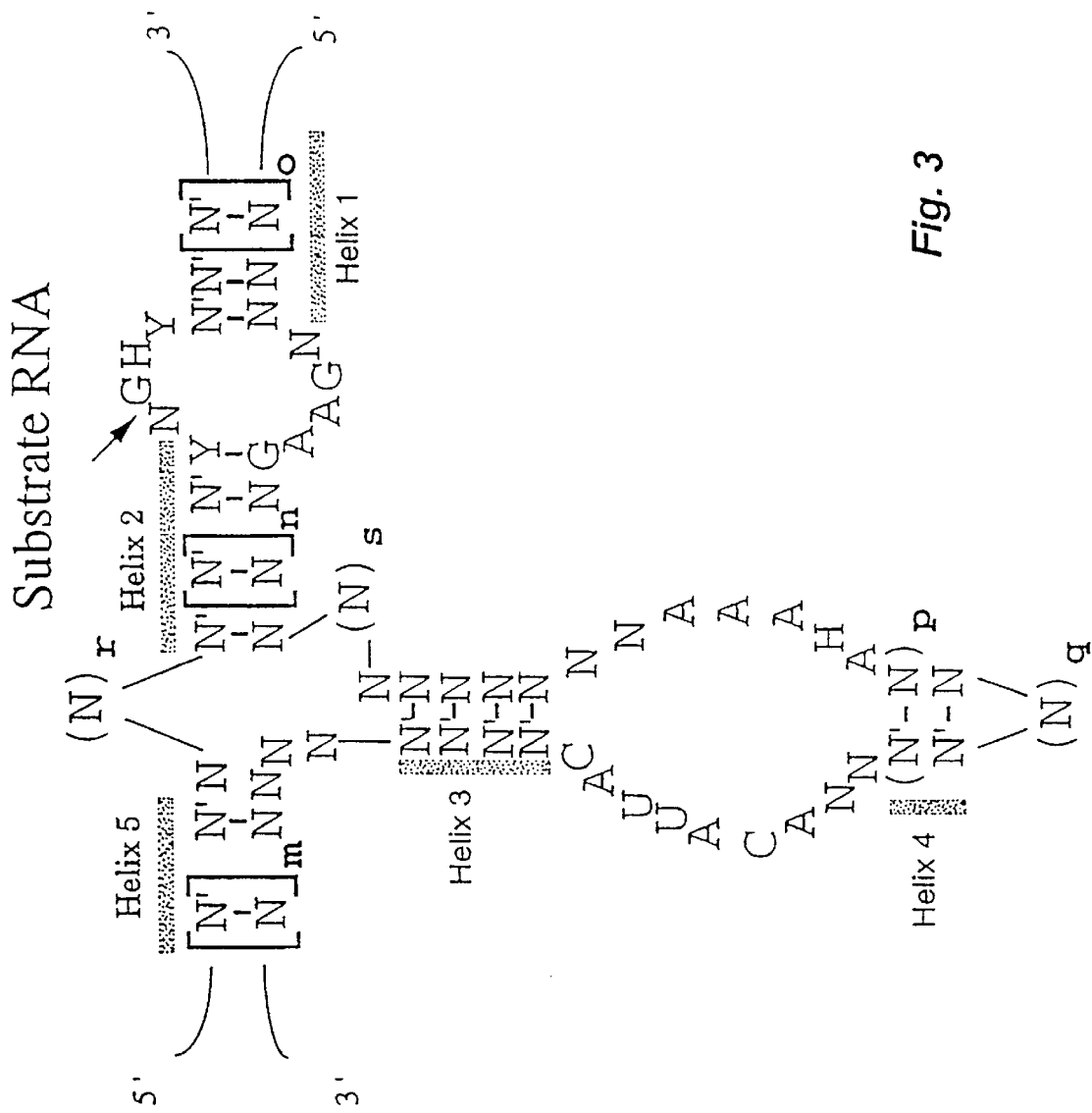
Figure 4:
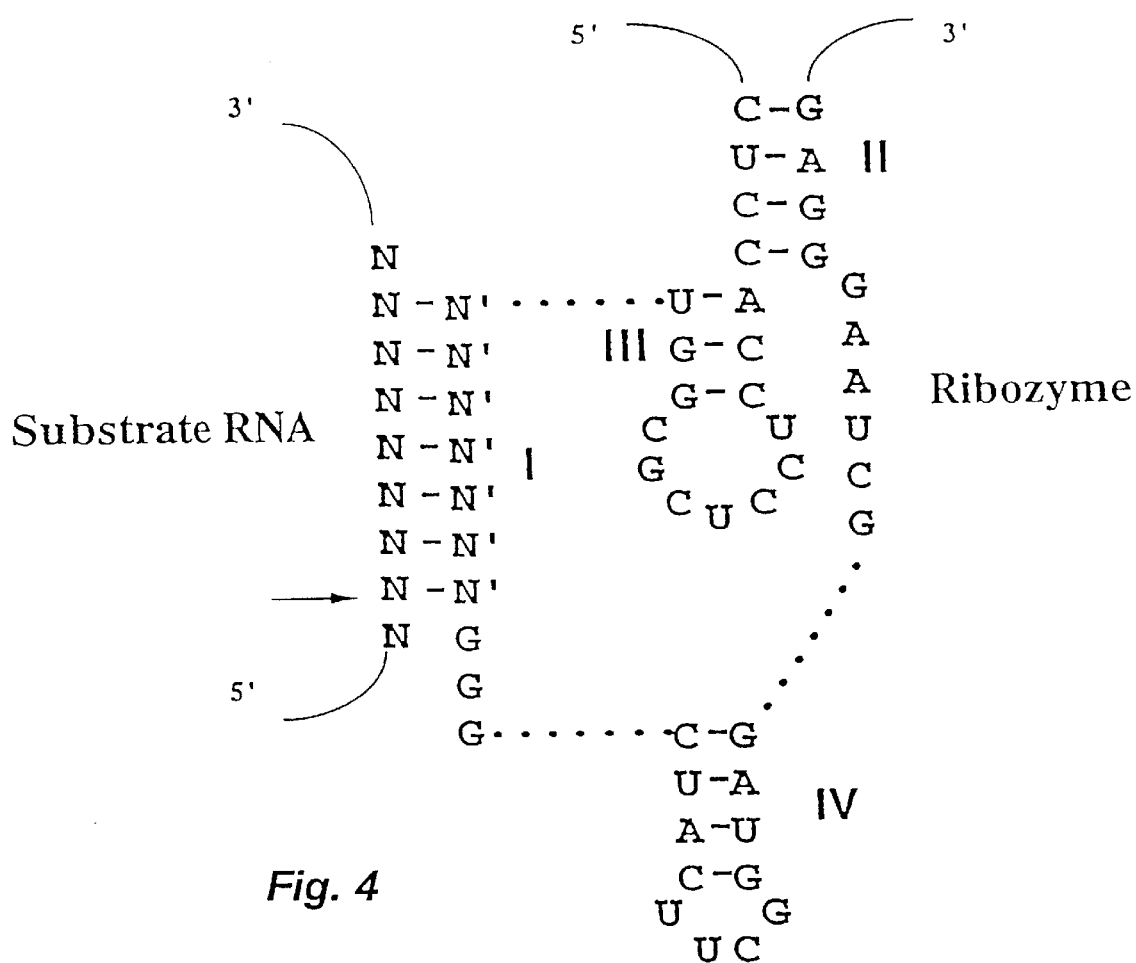
FIG. 4 is a representation of the general structure of the hepatitis delta virus ribozyme domain known in the art.
Figure 5:
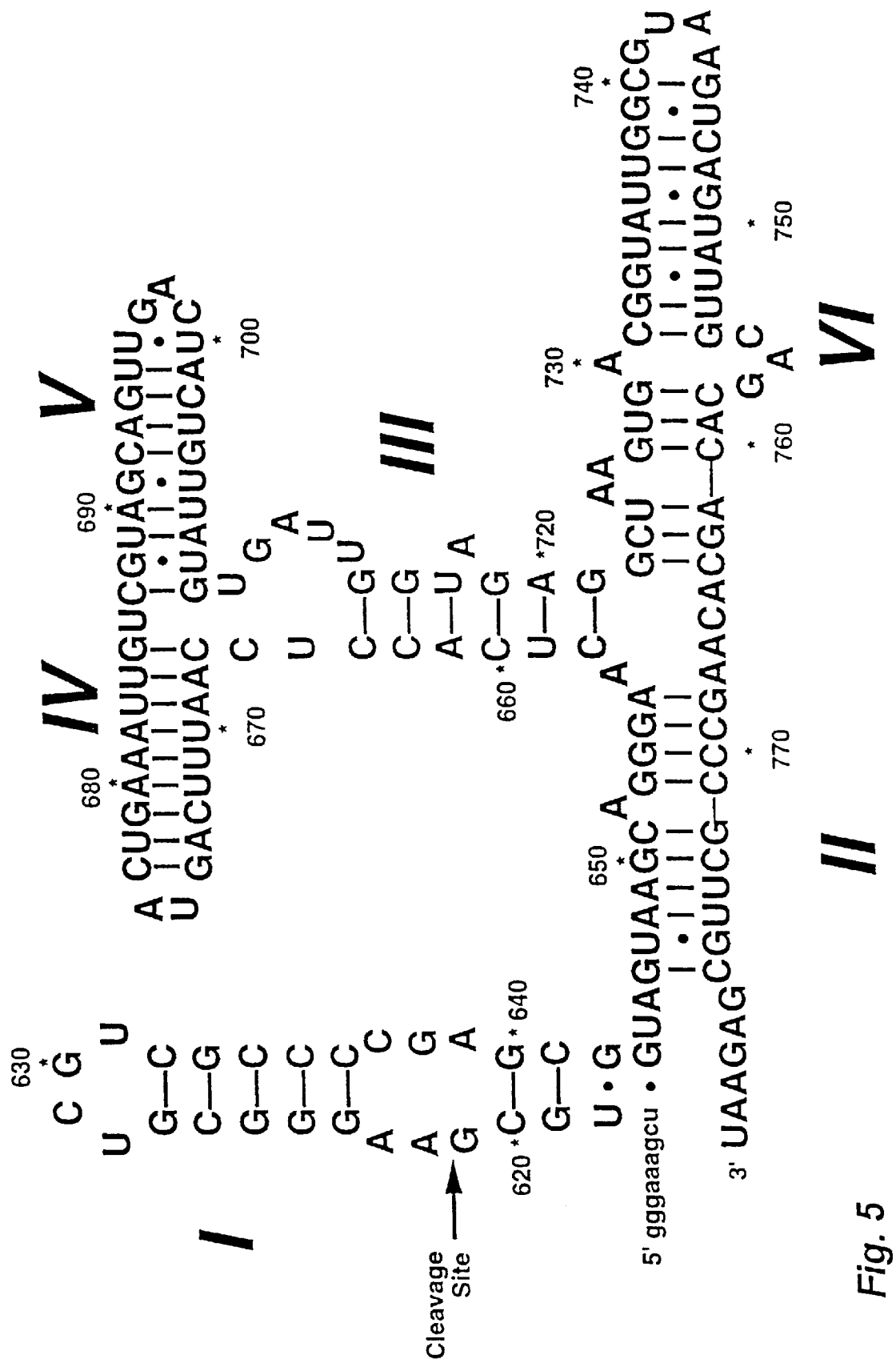
FIG. 5 is a representation of the general structure of the self-cleaving VS RNA ribozyme domain.

Ribozyme activity can be optimized as described by Draper et al., supra. The details will not be repeated here, but include altering the length of the ribozyme binding arms (stems I and III, see FIG. 2c), or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of stem II bases to shorten RNA synthesis times and reduce chemical requirements are desired. (All these publications are hereby incorporated by reference herein.).

By "enhanced enzymatic activity" is meant to include activity measured in cells and/or in vivo where the activity is a reflection of both catalytic activity and ribozyme stability. In this invention, the product of these properties in increased or not significantly (less that 10 fold) decreased in vivo compared to an all RNA ribozyme.

The enzymatic nucleic acid having chemical modifications which maintain or enhance enzymatic activity is provided. Such nucleic acid is also generally more resistant to nucleases than unmodified nucleic acid. By "modified bases" in this aspect is meant nucleotide bases other than adenine, guanine, cytosine and uracil at 1' position or their equivalents; such bases may be used within the catalytic core of the enzyme as well as in the substrate-binding regions. In particular, the invention features modified ribozymes having a base substitution selected from pyridin-4-one, pyridin-2-one, phenyl, pseudouracil, 2,4,6-trimethoxy benzene, 3-methyluracil, dihydrouracil, naphthyl, 6-methyl-uracil and aminophenyl. As noted above, substitution in the core may decrease in vitro activity but enhances stability. Thus, in a cell and/or in vivo the activity may not be significantly lowered. As exemplified herein such ribozymes are useful in a cell and/or in vivo even if activity over all is reduced 10 fold. Such ribozymes herein are said to "maintain" the enzymatic activity on all RNA ribozyme.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. USA.*, 90, 8000–4; Thompson et al., 1995 *Nucleic Acids Res.* 23, 2259). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In a preferred embodiment of the invention, a transcription unit expressing a ribozyme that cleaves mRNAs encoded by c-fos is inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo. Retroviral vectors have also been used to express ribozymes in mammalian cells (Ojwang et al., 1992 supra; Thompson et al., 1995 supra; Couture and Stinchcomb, 1996, supra).

In another preferred embodiment, the ribozyme is administered to the site of c-fos expression (e.g., tumor cells) in an appropriate liposomal vesicle.

EXAMPLES

Ability of Ribozymes Directed Against c-fos RNA to Modulate Gene Expression and Cell Proliferation The following examples demonstrate the selection of ribozymes that cleave c-fos RNA. The methods described herein represent a scheme by which ribozymes may be derived that cleave other RNA targets required for cell division. Also provided is a description of how such ribozymes may be delivered to cells. The examples demonstrate that upon delivery, the ribozymes inhibit cell proliferation in culture and modulate gene expression in vivo. Moreover, significantly reduced inhibition is observed if mutated ribozymes that are catalytically inactive are applied to the cells. Thus, inhibition requires the catalytic activity of the ribozymes.

Example 1

Identification of Potential Ribozyme Cleavage Sites in Human c-fos RNA

The sequence of human c-fos RNA was screened for accessible sites using a computer folding algorithm. Regions of the mRNA that did not form secondary folding structures and contained potential hammerhead and/or hairpin ribozyme cleavage sites were identified. The sequences of these cleavage sites are shown in tables III and IV.

Example 2
Selection of Ribozyme Cleavage Sites in Human c-fos RNA

To test whether the sites predicted by the computer-based RNA folding algorithm corresponded to accessible sites in c-fos RNA, 14 hammerhead sites were selected for analysis. Ribozyme target sites were chosen by analyzing genomic sequences of human c-fos (GenBank Accession No. K00650 and GenBank Accession No. M16287, respectively; van Straaten et al., 1983, *Proc. Natl. Acad. Sci. USA*, 80, 3183) and prioritizing the sites on the basis of folding. Hammerhead ribozymes were designed that could bind each target (see FIG. 2C) and were individually analyzed by computer folding (Christoffersen et al., 1994 *J. Mol. Struc. Theochem*, 311, 273; Jaeger et al., 1989, *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 3
Chemical Synthesis and Purification of Ribozymes for Efficient Cleavage of c-fos RNA Ribozymes of the hammerhead or hairpin motif were designed to anneal to various sites in the RNA message. The binding arms are complementary to the target site sequences described above. The ribozymes were chemically synthesized. The method of synthesis used followed the procedure for normal RNA synthesis as described in Usman et al., (1987 *J. Am. Chem. Soc.*, 109, 7845), Scaringe et al., (1990 *Nucleic Acids Res.*, 18, 5433) and Wincott et al., supra, and made use of common nucleic acid protecting and coupling groups, such as dimethoxytrityl at the 5'-end, and phosphoramidites at the 3'-end. The average stepwise coupling yields were >98%. Inactive ribozymes were synthesized by substituting a U for $G_5$ and a U for $A_{14}$ (numbering from Hertel et al., 1992 *Nucleic Acids Res.*, 20, 3252). Hairpin ribozymes were synthesized in two parts and annealed to reconstruct the active ribozyme (Chowrira and Burke, 1992 *Nucleic Acids Res.*, 20, 2835–2840). Ribozymes were also synthesized from DNA templates using bacteriophage T7 RNA polymerase (Milligan and Uhlenbeck, 1989, *Methods Enzymol.* 180, 51). All ribozymes were modified to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34). Ribozymes were purified by gel electrophoresis using general methods or were purified by high pressure liquid chromatography (HPLC; See Wincott et al., supra; the totality of which is hereby incorporated herein by reference) and were resuspended in water. The sequences of the chemically synthesized ribozymes used in this study are shown below in Table III and IV.

Example 4
Ribozyme Cleavage of c-fos RNA Target

Fourteen hammerhead-type ribozymes targeted to the human c-fos RNA were designed and synthesized to test the cleavage activity in vitro. The target sequences and the nucleotide location within the c-fos mRNA are given in Table III. All hammerhead ribozymes were synthesized with binding arm (Stems I and III; see FIG. 2C) lengths of seven nucleotides. The relative abilities of these ribozymes to cleave human c-fos RNA is summarized in FIG. 6.

Full-length or partially full-length, internally-labeled target RNA for ribozyme cleavage assay was prepared by in vitro transcription in the presence of [$\alpha$-$^{32}$p]CTP, passed over a G 50 Sephadex column by spin chromatography and used as substrate RNA without further purification. Alternately, substrates were 5'-$^{32}$P-end labeled using T4 polynucleotide kinase enzyme. Assays were performed by pre-warming a 2× concentration of purified ribozyme in ribozyme cleavage buffer (50 mM Tris-HCl, pH 7.5 at 37° C., 10 mM $MgCl_2$) and the cleavage reaction was initiated by adding the 2×ribozyme mix to an equal volume of substrate RNA (maximum of 1–5 nM) that was also pre-warmed in cleavage buffer. As an initial screen, assays were carried out for 1 hour at 37° C. using a final concentration of either 40 nM or 1 $\mu$M ribozyme, i.e., ribozyme excess. The reaction was quenched by the addition of an equal volume of 95% formamide, 20 mM EDTA, 0.05% bromophenol blue and 0.05% xylene cyanol after which the sample was heated to 95° C. for 2 minutes, quick chilled and loaded onto a denaturing polyacrylamide gel. Substrate RNA and the specific RNA cleavage products generated by ribozyme cleavage were visualized on an autoradiograph of the gel. The percentage of cleavage was determined by Phosphor Imager® quantitation of bands representing the intact substrate and the cleavage products.

Figure 6:
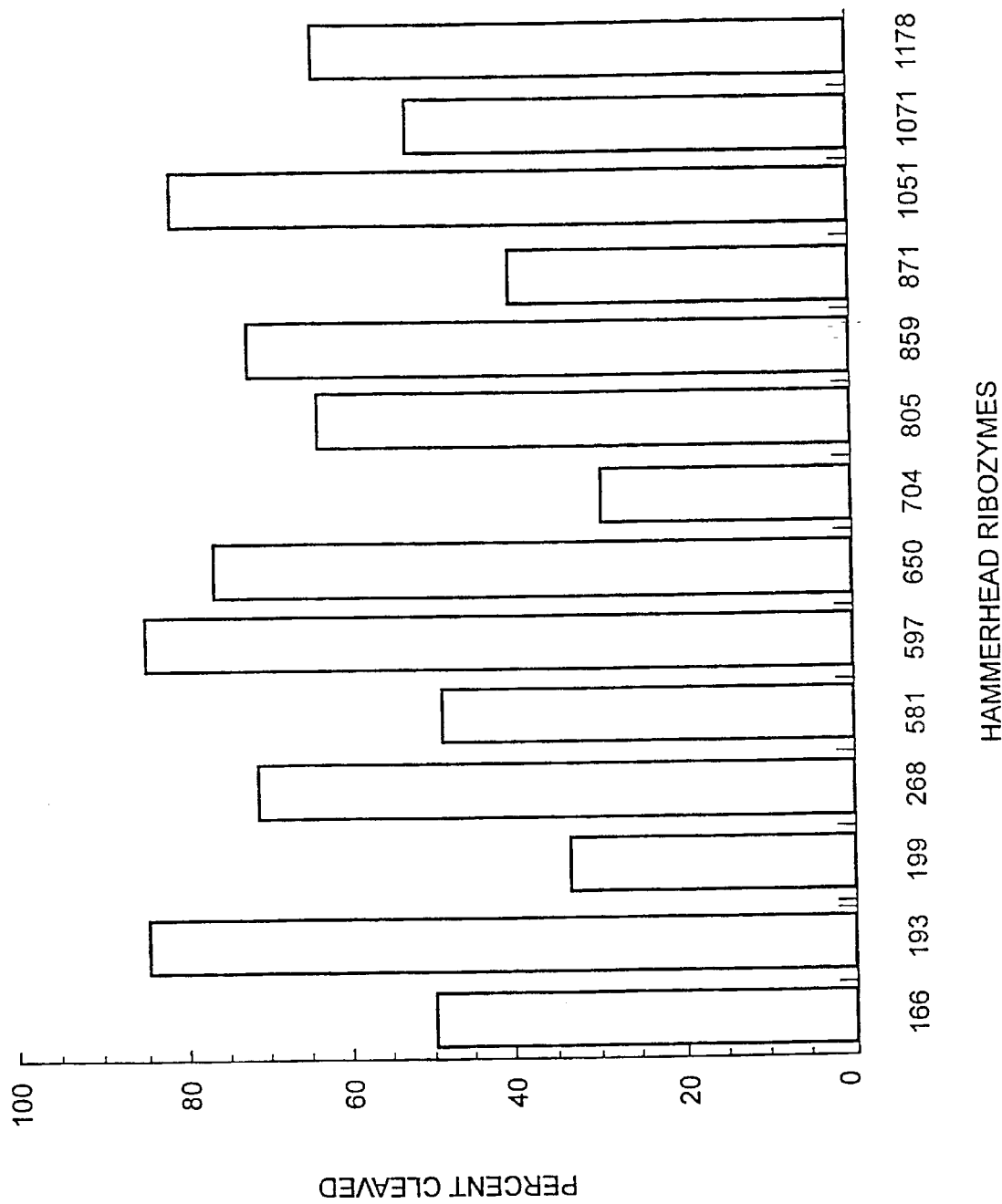
FIG. 6 is a graphical representation of results of an RNA cleavage reaction catalyzed by ribozymes targeted against c-fos RNA at the indicated sites. Numbers 163–1178 are meant to indicate examples of nucleotide sites within c-fos RNA that are targeted for ribozyme cleavage.

As shown in FIG. 6, all 14 hammerhead ribozymes cleaved their target RNAs in a sequence-specific manner.

Example 5
Ability of c-fos Ribozymes to Inhibit Smooth Muscle Cell Proliferation The ribozymes that cleaved c-fos RNA described above were assayed for their effect on smooth muscle cell proliferation. Human vascular smooth muscle cells were isolated and cultured as follows. Human aortic smooth muscle cells (AOSMC) were obtained from Clonetics and were grown in SmGM (Clonetics®). Cells from passage five or six were used for assays. For the cell proliferation assays, 24-well tissue culture plates were prepared by coating the wells with 0.2% gelatin and washing once with phosphate-buffered saline (PBS). AOSMC were inoculated at 1×$10^4$ cells per well in 1 ml of SmGM plus 10% FBS and additives and incubated for 24 hours. The cells were subconfluent when plated at this density. The cells were serum-starved by removing the medium, washing once with PBS, and incubating 48–72 hours in SmBM plus 0.5% FBS.

In several other systems, cationic lipids have been shown to enhance the bioavailability of oligonucleotides to cells in culture (Bennet, C. F., et al., 1992, *Mol. Pharmacology*, 41, 1023–1033). In many of the following experiments, ribozymes were complexed with cationic lipids. The cationic lipid, Lipofectamine (a 3:1 (w/w) formulation of DOSPA (2,3-dioleyloxy-N-[2(sperminecarboxamido)ethyl]-N,N-dimethyl-1-propanaminium trifluoroacetate) and dioleoyl phosphatidylethanolamine (DOPE)), was purchased from Life Technologies, Inc. DMRIE (N-[1-(2,3-ditetradecyloxy)propyl]-N,N-dimethyl-N-hydroxyethylammonium bromide) was obtained from VICAL. DMRIE was resuspended in $CHCl_3$ and mixed at a 1:1 molar ratio with dioleoyl phosphatidylethanolamine (DOPE). The $CHCl_3$ was evaporated, the lipid was resuspended in water, vortexed for 1 minute and bath sonicated for 5 minutes. Ribozyme and cationic lipid mixtures were prepared in serum-free DMEM immediately prior to addition to the cells. DMEM plus additives was warmed to room temperature (about 20–25° C.), cationic lipid was added to the final desired concentration and the solution was vortexed briefly. RNA oligonucleotides were added to the final desired concentration and the solution was again vortexed briefly and incubated for 10 minutes at room temperature. In dose response experiments, the RNA/lipid complex was serially diluted into DMEM following the 10 minute incubation.

Serum-starved smooth muscle cells were washed twice with PBS, and the RNA/lipid complex was added. The plates were incubated for 4 hours at 37° C. The medium was then removed and DMEM containing 10% FBS, additives and 10 $\mu$M bromodeoxyuridine (BrdU) was added. In some wells, FBS was omitted to determine the baseline of unstimulated proliferation. The plates were incubated at 37° C. for 20–24 hours, fixed with 0.3% $H_2O_2$ in 100% methanol, and stained for BrdU incorporation by standard methods. In this procedure, cells that have proliferated and incorporated BrdU stain brown; non-proliferating cells are counterstained a light purple. Both BrdU positive and BrdU negative cells were counted under the microscope. 300–600 total cells per well were counted. In the following experiments, the percentage of the total cells that have incorporated BrdU (% cell proliferation) is presented. Errors represent the range of duplicate wells. Percent inhibition then is calculated from the % cell proliferation values as follows: % inhibition= 100−100((Ribozyme−0% serum)/(Control−0% serum)).

Figure 7:
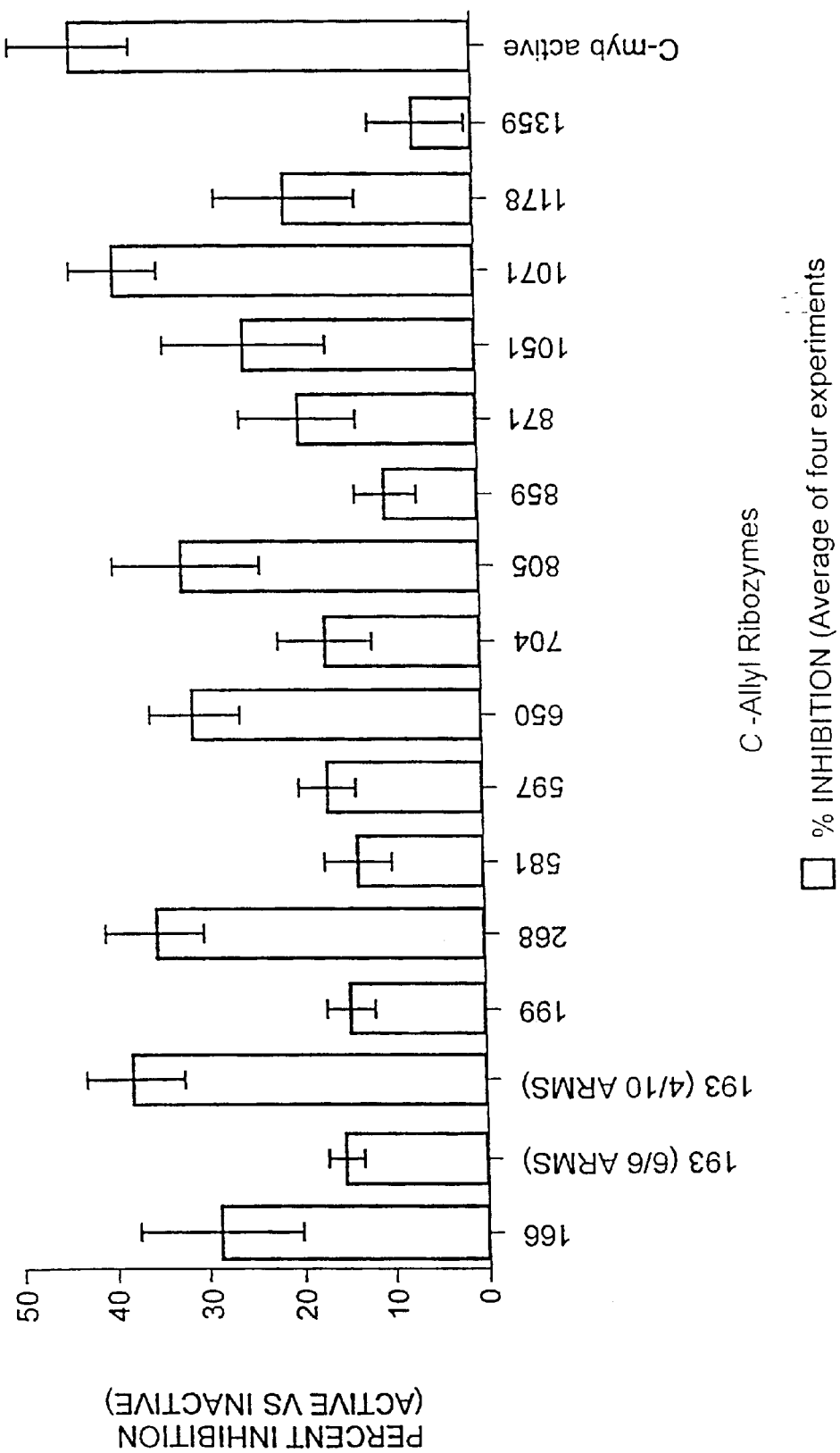
FIG. 7 is a graphical representation of c-fos c-allyl ribozyme-mediated inhibition of cell proliferation. Numbers 166–1359 are meant to indicate examples of nucleotide sites within c-fos RNA that are targeted for ribozyme cleavage. 6/6 and 4/10 arms, are meant to indicate the number of nucleotides in each of the two binding arms of a hammerhead ribozyme targeted against site 193.

Fifteen stabilized hammerhead ribozymes with C-allyl modification (see FIG. 9B) were delivered at a concentration of 0.3 $\mu$M, complexed with DMRIE/DOPE such that the cationic lipid charges and the anionic RNA charges were at 1:1 molar ratio. The results, shown in FIG. 7, demonstrate the efficacy of ribozymes directed against different sites within c-fos RNA. The control, inactive ribozymes that cannot cleave c-fos RNA due to alterations in their catalytic core sequence fail to inhibit smooth muscle cell proliferation. Thus, inhibition of cell proliferation by these hammerhead sequences is due to their ability to cleave c-fos RNA, and not because of any non-ribozyme activity.

Figure 8:
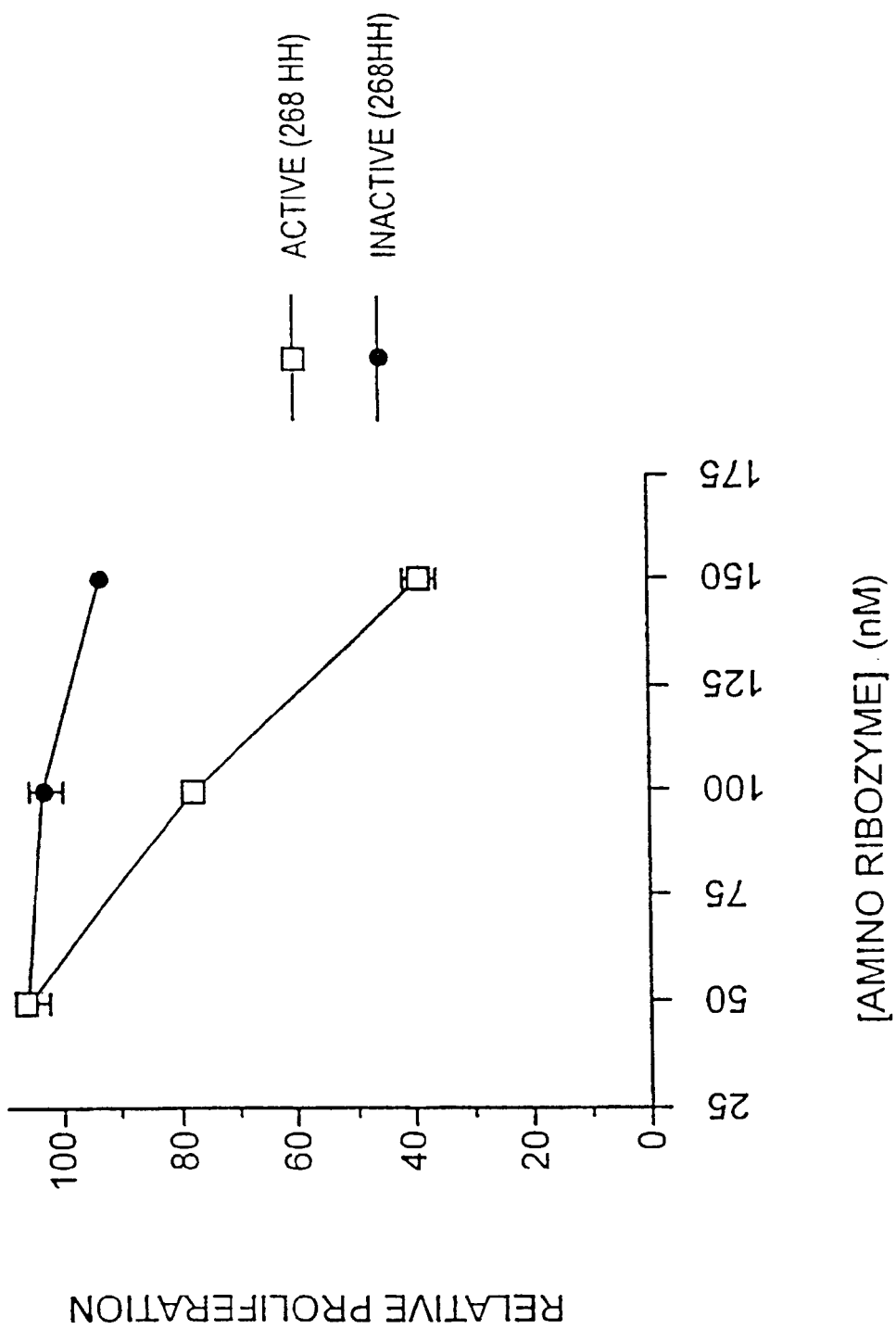
FIG. 8 is a graphical representation of c-fos amino ribozyme-mediated inhibition of cell proliferation.

Example 6
Ribozymes Inhibit Proliferation of Smooth Muscle Cells in a Dose-dependent Fashion If the inhibition of proliferation observed in Example 5 is caused by the ribozymes, the level of inhibition should be proportional to the dose of RNA added. Human aortic smooth muscle cells were assayed for proliferation in the presence of differing doses of an amino (see FIG. 9A) site 268 hammerhead ribozymes. The result shown in FIG. 8, indicates that two hammerhead ribozymes that cleave c-fos RNA at sites 268 inhibit SMC proliferation in a dose-dependent fashion. Ribozymes were delivered with the cationic lipid, Lipofectamine at a 1:1 charge ratio. In this experiment, 10% FBS (no ribozyme) gave 92±1% proliferation; 0% FBS gave 6±1% proliferation. The control is an inactive ribozyme and shows no inhibition over the dose range tested. The control ribozyme contains the same catalytic core sequences as the active ribozymes but differs in its catalytic core sequence. Thus, ribozyme inhibition of smooth muscle cell proliferation requires sequence-specific binding and cleavage by the hammerhead ribozymes targeted against c-fos RNA.

Example 7
Modulation of Stromelysin Gene Expression in Rabbit Knee by c-fos Ribozyme.

In order to extend the ribozyme efficacy in cell culture, applicant has chosen to use rabbit knee as a reasonable animal model to study ribozyme-mediated inhibition of rabbit stromelysin protein expression. Applicant selected a amino hammerhead (HH) ribozyme (268 Amino Ribozyme), targeted to site 268 within human c-fos RNA, for animal studies. This has enabled applicant to compare the efficacy of the same ribozyme in human as well as in rabbit systems.

Male New Zealand White Rabbits (3–4 Kg) were anaesthetized with ketamine-HCl/xylazine and injected intraarticularly (I.T.) in both knees with 100 $\mu$g ribozyme (268 Amino Ribozyme) in 0.5 ml phosphate buffered saline (PBS) or PBS alone (Controls). The IL-1 (human recombinant IL-1$\alpha$, 25 ng) was administered I.T., 24 hours following the ribozyme administration. Each rabbit received IL-1 in one knee and PBS alone in the other. The synovium was harvested 6 hours post IL-1 infusion, snap frozed in liquid nitrogen, and stored at −80° C. Total RNA is extracted with TRIzol reagent (GIBCO BRL, Gaithersburg, Md.), and was analyzed by Northern-blot analysis and/or RNase-protection assay. Briefly, 0.5 $\mu$g cellular RNA was separated on 1.0% agarose/formaldehyde gel and transferred to Zeta-Probe GT nylon membrane (Bio-Rad, Hercules, Calif.) by capillary transfer for ~16 hours. The blots were baked for two hours and then pre-hybridized for 2 hours at 65° C. in 10 ml Church hybridization buffer (7% SDS, 500 mM phosphate, 1 mM EDTA, 1% Bovine Serum Albumin). The blots were hybridized at 65° C. for ~16 hours with $10^6$ cpm/ml of full length $^{32}$P-labeled complementary RNA (cRNA) probes to rabbit stromelysin mRNA (cRNA added to the pre-hybridization buffer along with 100 $\mu$l 10 mg/ml salmon sperm DNA). The blot was rinsed once with 5% SDS, 25 mM phosphate, 1 mM EDTA and 0.5% BSA for 10 min at room temperature. This was followed by two washes (10 min each wash) with the same buffer at 65° C., which was then followed by two washes (10 min each wash) at 65° C. with 1% SDS, 25 mM phosphate and 1 mM EDTA. The blot was autoradiographed. The blot was reprobed with a 100 nt cRNA probe to 18S rRNA as described above. Following autoradiography, the stromelysin expression was quantified on a scanning densitometer, which is followed by normalization of the data to the 18S rRNA band intensities.

As shown in Table V, catalytically active 268 Amino Ribozyme mediates a decrease in the expression of stromelysin RNA in rabbit knees. The inhibition appears to be sequence-specific and ranges from 40–47%.

Optimizing Ribozyme Activity

Sullivan, et al., supra, describes the general methods for delivery of enzymatic RNA molecules. The data presented in Examples above indicate that different cationic lipids can deliver active ribozymes to smooth muscle cells. Experiments similar to those performed in above-mentioned Examples are used to determine which lipids give optimal delivery of ribozymes to specific cells. Other such delivery methods are known in the art and can be utilized in this invention.

The proliferation of smooth muscle cells can also be inhibited by the direct addition of chemically stabilized ribozymes. Presumably, uptake is mediated by passive diffusion of the anionic nucleic acid across the cell membrane. In this case, efficacy could be greatly enhanced by directly coupling a ligand to the ribozyme. The ribozymes are then delivered to the cells by receptor-mediated uptake. Using such conjugated adducts, cellular uptake can be increased by several orders of magnitude without having to alter the phosphodiester linkages necessary for ribozyme cleavage activity.

Alternatively, ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intramuscular injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Chemical modifications, ribozyme sequences and ribozyme motifs described in this invention are meant to be non-limiting examples, and those skilled in the art will recognize that other modifications (base, sugar and phosphate modifications) to enhance nuclease stability of a ribozyme can be readily generated using standard techniques and are hence within the scope of this invention.

Use of Ribozymes Targeting c-fos

Overexpression of the c-fos oncogene has been reported in a number of cancers (see above). Thus, inhibition of c-fos expression (for example using ribozymes) can reduce cell proliferation of a number of cancers, in vitro and in vivo and can reduce their proliferative potential. A cascade of MMP and serine proteinase expression is implicated in the acquisition of an invasive phenotype as well as in angiogenesis in tumors (MacDougall & Matrisian, 1995, *Cancer & Metastasis Reviews* 14, 351; Ritchlin & Winchester, 1989, *Springer Semin Immunopathol.*, 11, 219).

Ribozymes, with their catalytic activity and increased site specificity (see above), are likely to represent a potent and safe therapeutic molecule for the treatment of cancer. In the present invention, ribozymes are shown to inhibit smooth muscle cell proliferation and stromelysin gene expression. From those practiced in the art, it is clear from the examples described, that the same ribozymes may be delivered in a similar fashion to cancer cells to block their proliferation.

Chronic wound healing: Metalloproteinase expression is undetectable in normal epidermis, but is stimulated upon wounding. Although protease expression is required for tissue remodelling in normal wound healing, it is likely than excessive proteolytic activity contributes to the pathology of chronic ulcers. Collagenase expression in basal keratinocytes at the advancing edge of wounds is correlated with degree of ulceration (Saarialho-Kere et al., 1992, *J. Clin. Invest.* 90:1952) and has been implicated in the pathophysiology of chronic blistering disease, recessive dystrophic epidermolysis bullosa and skin cancer (Lin et al., 1995, *FASEB J.* 9, 1371–77). Stromelysin 1 and 2 are both expressed by keratinocytes in a variety of chronic ulcers. Since c-fos regulates the expression of all of these MMPs, ribozymes targeting c-fos could potentially lead to enhanced re-epithelialization of ulcers.

Arthritis: Matrix metalloproteinases have frequently been implicated in the degradation of cartilage associated with both rheumatoid and osteoarthritis (Hembry et al., 1995, *Ann. Rheum. Dis.*, 54, 25–32; Okada et al., 1992, *Lab. Invest.* 66, 680). Since multiple MMPs appear to contribute to the destructive phenotype, the ability to inhibit the entire MMP family would be desirable. In addition, c-fos has been shown to be required for MHC class I expression (Kushtai et al., 1988, *Oncogene* 2, 119). Thus, inhibition of c-fos expression by ribozymes would likely reduce both the cartilage catabolism associated with MMP expression and also the underlying immune response triggering rheumatoid arthritis. C-fos ribozymes therefore show considerable promise as therapeutics for arthritis.

Diagnostic Uses

Ribozymes of this invention may be used as diagnostic tools to examine genetic drift and mutations within diseased cells or to detect the presence of c-fos RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with c-fos related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., c-fos) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Naturally Occurring Ribozymes

Group I Introns

Size: ~150 to >1000 nucleotides.

Requires a U in the target sequence immediately 5' of the cleavage site.

Binds 4–6 nucleotides at the 5'-side of the cleavage site.

Reaction mechanism: attack by the 3'-OH of guanosine to generate cleavage products with 3'-OH and 5'-guanosine.

Additional protein cofactors required in some cases to help folding and maintainance of the active structure [1].

Over 300 known members of this class. Found as an intervening sequence in *Tetrahymena thermophila* rRNA, fungal mitochondria, chloroplasts, phage T4, blue-green algae, and others.

Major structural features largely established through phylogenetic comparisons, mutagenesis, and biochemical studies [2,3].

Complete kinetic framework established for one ribozyme [4,5,6,7].

Studies of ribozyme folding and substrate docking underway [8,9,10].

Chemical modification investigation of important residues well established [11,12].

The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].

RNAse P RNA (M1 RNA)

Size: ~290 to 400 nucleotides.

RNA portion of a ubiquitous ribonucleoprotein enzyme.

Cleaves tRNA precursors to form mature tRNA [14].

Reaction mechanism: possible attack by $M^{2+}$-OH to generate cleavage products with 3'-OH and 5'-phosphate.

RNAse P is found throughout the prokaryotes and eukaryotes. The RNA subunit has been sequenced from bacteria, yeast, rodents, and primates.

Recruitment of endogenous RNAse P for therapeutic applications is possible through hybridization of an External Guide Sequence (EGS) to the target RNA [15,16].

Important phosphate and 2' OH contacts recently identified [17,18].

Group II Introns

Size: >1000 nucleotides.

Trans cleavage of target RNAs recently demonstrated [19,20].

Sequence requirements not fully determined.

Reaction mechanism: 2'-OH of an internal adenosine generates cleavage products with 3'-OH and a "lariat" RNA containing a 3'-5' and a 2'-5' branch point.

Only natural ribozyme with demonstrated participation in DNA cleavage [21,22] in addition to RNA cleavage and ligation.

Major structural features largely established through phylogenetic comparisons [23].

Important 2' OH contacts beginning to be identified [24].

Kinetic framework under development [25].

Neurospora VS RNA

Size: ~144 nucleotides.

Trans cleavage of hairpin target RNAs recently demonstrated [26].

Sequence requirements not fully determined.

Reaction mechanism: attack by 2'-OH 5' to the scissile bond to generate cleavage products with 2',3'-cyclic phosphate and 5'-OH ends.

Binding sites and structural requirements not fully determined.

Only 1 known member of this class. Found in Neurospora VS RNA.

Hammerhead Ribozyme
(see text for references)

Size: ~13 to 40 nucleotides.

Requires the target sequence UH immediately 5' of the cleavage site.

Binds a variable number nucleotides on both sides of the cleavage site.

Reaction mechanism: attack by 2'-OH 5' to the scissile bond to generate cleavage products with 2',3'-cyclic phosphate and 5'-OH ends.

14 known members of this class. Found in a number of plant pathogens (virusoids) that use RNA as the infectious agent.

Essential structural features largely defined, including 2 crystal structures [ ].

Minimal ligation activity demonstrated (for engineering through in vitro selection) [ ].

Complete kinetic framework established for two or more ribozymes [ ].

Chemical modification investigation of important residues well established [ ].

Hairpin Ribozyme

Size: ~50 nucleotides.

Requires the target sequence GUC inunediately 3' of the cleavage site.

Binds 4–6 nucleotides at the 5'-side of the cleavage site and a variable number to the 3'-side of the cleavage site.

Reaction mechanism: attack by 2'-OH 5' to the scissile bond to generate cleavage products with 2',3'-cyclic phosphate and 5'-OH ends.

3 known members of this class. Found in three plant pathogen (satellite RNAs of the tobacco ringspot virus, arabis mosaic virus and chicory yellow mottle virus) which uses RNA as the infectious agent.

Essential structural features largely defined [27,28,29,30]

Ligation activity (in addition to cleavage activity) makes ribozyme amenable to engineering through in vitro selection [31].

Complete kinetic framework established for one ribozyme [32].

Chemical modification investigation of important residues begun [33,34].

Hepatitis Delta Virus (HDV) Ribozyme

Size: ~60 nucleotides.

Trans cleavage of target RNAs demonstrated [35].

Binding sites and structural requirements not fully determined, although no sequences 5' of cleavage site are required. Folded ribozyme contains a pseudoknot structure [36].

Reaction mechanism: attack by 2'-OH 5' to the scissile bond to generate cleavage products with 2',3'-cyclic phosphate and 5'-OH ends.

Only 2 known members of this class. Found in human HDV.

Circular form of HDV is active and shows increased nuclease stability [37].

1. Mohr, G.; Caprara, M. G.; Guo, Q.; Lambowitz, A. M. Nature, 370 147–150 (1994).

2. Michel, Francois; Westhof, Eric. Slippery substrates. Nat. Struct. Biol. (1994), 1(1), 5–7.
3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R. Catalysis of RNA cleavage by the Tetrahymena thermophila ribozyme. 1. Kinetic description of the reaction of an RNA substrate complementary to the active site. Biochemistry (1990), 29(44), 10159–71.
5. Herschlag, Daniel; Cech, Thomas R. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Turner, Douglas H. A mechanistic framework for the second step of splicing catalyzed by the Tetrahymena ribozyme. Biochemistry (1996), 35(2), 648–58.
8. Li, Yi; Bevilacqua, Philip C.; Mathews, David; Turner, Douglas H. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
9. Banerjee, Aloke Raj; Turner, Douglas H. The time dependence of chemical modification reveals slow steps in the folding of a group I ribozyme. Biochemistry (1995), 34(19), 6504–12.
10. Zarrinkar, Patrick P.; Williamson, James R. The P9.1–P9.2 peripheral extension helps guide folding of the Tetrahymena ribozyme. Nucleic Acids Res. (1996), 24(5), 854–8.
11. Strobel, Scott A.; Cech, Thomas R. Minor groove recognition of the conserved G.cntdot.U pair at the Tetrahymena ribozyme reaction site. Science (Washington, D.C.) (1995), 267(5198), 675–9.
12. Strobel, Scott A.; Cech, Thomas R. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R. Ribozyme-mediated repair of defective mRNA by targeted trans-splicing. Nature (London) (1994), 371(6498), 619–22.
14. Robertson, H. D.; Altman, S.; Smith, J. D. J. Biol. Chem., 247, 5243–5251 (1972).
15. Forster, Anthony C.; Altman, Sidney. External guide sequences for an RNA enzyme. Science (Washington, D.C., 1883-) (1990), 249(4970), 783–6.
16. Yuan, Y.; Hwang, E. S.; Altman, S. Targeted cleavage of mRNA by human RNase P. Proc. Natl. Acad. Sci. USA (1992) 89, 8006–10.
17. Harris, Michael E.; Pace, Norman R. Identification of phosphates involved in catalysis by the ribozyme RNase P RNA. RNA (1995), 1(2), 210–18.
18. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
19. Pyle, Anna Marie; Green, Justin B. Building a Kinetic Framework for Group II Intron Ribozyme Activity: Quantitation of Interdomain Binding and Reaction Rate. Biochemistry (1994), 33(9), 2716–25.
20. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M. A group II intron RNA is a catalytic component of a DNA endonuclease involved in intron mobility. Cell (Cambridge, Mass.) (1995), 83(4), 529–38.
22. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
26. Guo, Hans C. T.; Collins, Richard A. Efficient trans-cleavage of a stem-loop RNA substrate by a ribozyme derived from Neurospora VS RNA. EMBO J. (1995), 14(2), 368–76.
27. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
28. Chowrira, Bharat M.; Berzal-Herranz, Alfredo; Burke, John M. Novel guanosine requirement for catalysis by the hairpin ribozyme. Nature (London) (1991), 354(6351), 320–2.
29. Berzal-Herranz, Alfredo; Joseph, Simpson; Chowrira, Bharat M.; Butcher, Samuel E.; Burke, John M. Essential nucleotide sequences and secondary structure elements of the hairpin ribozyme. EMBO J. (1993), 12(6), 2567–73.
30. Joseph, Simpson; Berzal-Herranz, Alfredo; Chowrira, Bharat M.; Butcher, Samuel E. Substrate selection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M. In vitro selection of active hairpin ribozymes by sequential RNA-catalyzed cleavage and ligation reactions. Genes Dev. (1992), 6(1), 129–34.
32. Hegg, Lisa A.; Fedor, Martha J. Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michael J. Purine Functional Groups in Essential Residues of the Hairpin Ribozyme Required for Catalytic Cleavage of RNA. Biochemistry (1995), 34(12), 4068–76.

34. Schmidt, Sabine; Beigelman, Leonid; Karpeisky, Alexander; Usman, Nassim; Sorensen, Ulrik S.; Gait, Michael J. Base and sugar requirements for RNA cleavage of essential nucleoside residues in internal loop B of the hairpin ribozyrne: implications for secondary structure. Nucleic Acids Res. (1996), 24(4), 573–81.
35. Perrotta, Anne T.; Been, Michael D. Cleavage of oligoribonucleotides by a ribozyme derived from the hepatitis .delta. virus RNA sequence. Biochemistry (1992), 31(1), 16–21.
36. Perrotta, Anne T.; Been, Michael D. A pseudoknot-like structure required for efficient self-cleavage of hepatitis delta virus RNA. Nature (London) (1991), 350(6317), 434–6.
37. Puttaraju, M.; Perrotta, Anne T.; Been, Michael D. A circular trans-acting hepatitis delta virus ribozyme. Nucleic Acids Res. (1993), 21(18), 4253–8.

TABLE II 2.5 µmol RNA Synthesis Cycle

| Reagent | Equivalents | Amount | Wait Time* |
|---|---|---|---|
| Phosphoramidites | 6.5 | 163 µL | 2.5 |
| S-Ethyl Tetrazole | 23.8 | 238 µL | 2.5 |
| Acetic Anhydride | 100 | 233 µL | 5 sec |
| N-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

TABLE III

Human C-fos Hammerhead Ribozyme and Target Sequences

| nt Position | Target site | SEQ. ID.NOS | Ribozyme Sequence | SEQ. ID.NOS |
|---|---|---|---|---|
| 9 | AACCGCAUC UGCAGCGA | 1 | UCGCUGCA CUGAUGA X GAA AUGCGGUU | 141 |
| 80 | ACCGUGCUC CUACCCAG | 2 | CUGGGUAG CUGAUGA X GAA AGCACGGU | 142 |
| 83 | GUGCUCCUA CCCAGCUC | 3 | GAGCUGGG CUGAUGA X GAA AGGAGCAC | 143 |
| 91 | ACCCAGCUC UGCUUCAC | 4 | GUGAAGCA CUGAUGA X GAA AGCUGGGU | 144 |
| 96 | GCUCUGCUU CACAGCGC | 5 | GCGCUGUG CUGAUGA X GAA AGCAGAGC | 145 |
| 97 | CUCUGCUUC ACAGCGCC | 6 | GGCGCUGU CUGAUGA X GAA AAGCAGAG | 146 |
| 113 | CCACCUGUC UCCGCCCC | 7 | GGGGCGGA CUGAUGA X GAA ACAGGUGG | 147 |
| 115 | ACCUGUCUC CGCCCCUC | 8 | GAGGGGCG CUGAUGA X GAA AGACAGGU | 148 |
| 123 | CCGCCCCUC GGCCCCUC | 9 | GAGGGGCC CUGAUGA X GAA AGGGGCGG | 149 |
| 131 | CGGCCCCUC GCCCGGCU | 10 | AGCCGGGC CUGAUGA X GAA AGGGGCCG | 150 |
| 140 | GCCCGGCUU UGCCUAAC | 11 | GUUAGGCA CUGAUGA X GAA AGCCGGGC | 151 |
| 141 | CCCGGCUUU GCCUAACC | 12 | GGUUAGGC CUGAUGA X GAA AAGCCGGG | 152 |
| 146 | CUUUGCCUA ACCGCCAC | 13 | GUGGCGGU CUGAUGA X GAA AGGCAAAG | 153 |
| 163 | GAUGAUGUU CUCGGGCU | 14 | AGCCCGAG CUGAUGA X GAA ACAUCAUC | 154 |
| 164 | AUGAUGUUC UCGGGCUU | 15 | AAGCCCGA CUGAUGA X GAA AACAUCAU | 155 |
| 172 | CUCGGGCUU CAACGCAG | 16 | CUGCGUUG CUGAUGA X GAA AGCCCGAG | 156 |
| 173 | UCGGGCUUC AACGCAGA | 17 | UCUGCGUU CUGAUGA X GAA AAGCCCGA | 157 |
| 184 | CGCAGACUA CGAGGCGU | 18 | ACGCCUCG CUGAUGA X GAA AGUCUGCG | 158 |
| 196 | GGCGUCAUC CUCCCGCU | 19 | AGCGGGAG CUGAUGA X GAA AUGACGCC | 159 |
| 199 | GUCAUCCUC CCGCUGCA | 20 | UGCAGCGG CUGAUGA X GAA AGGAUGAC | 160 |
| 217 | CAGCGCGUC CCCGGCCG | 21 | CGGCCGGG CUGAUGA X GAA ACGCGCUG | 161 |
| 231 | CCGGGGAUA GCCUCUCU | 22 | AGAGAGGC CUGAUGA X GAA AUCCCCGG | 162 |
| 236 | GAUAGCCUC UCUUACUA | 23 | UAGUAAGA CUGAUGA X GAA AGGCUAUC | 163 |
| 238 | UAGCCUCUC UUACUACC | 24 | GGUAGUAA CUGAUGA X GAA AGAGGCUA | 164 |
| 240 | GCCUCUCUU ACUACCAC | 25 | GUGGUAGU CUGAUGA X GAA AGAGAGGC | 165 |
| 241 | CCUCUCUUA CUACCACU | 26 | AGUGGUAG CUGAUGA X GAA AAGAGAGG | 166 |
| 244 | CUCUUACUA CCACUCAC | 27 | GUGAGUGG CUGAUGA X GAA AGUAAGAG | 167 |
| 250 | CUACCACUC ACCCGCAG | 28 | CUGCGGGU CUGAUGA X GAA AGUGGUAG | 168 |
| 262 | CGCAGACUC CUUCUCCA | 29 | UGGAGAAG CUGAUGA X GAA AGUCUGCG | 169 |
| 265 | AGACUCCUU CUCCAGCA | 30 | UGCUGGAG CUGAUGA X GAA AGGAGUCU | 170 |
| 266 | GACUCCUUC UCCAGCAU | 31 | AUGCUGGA CUGAUGA X GAA AAGGAGUC | 171 |
| 268 | CUCCUUCUC CAGCAUGG | 32 | CCAUGCUG CUGAUGA X GAA AGAAGGAG | 172 |
| 280 | CAUGGGCUC GCCUGUCA | 33 | UGACAGGC CUGAUGA X GAA AGCCCAUG | 173 |
| 287 | UCGCCUGUC AACGCGCA | 34 | UGCGCGUU CUGAUGA X GAA ACAGGCGA | 174 |
| 301 | GCAGGACUU CUGCACGG | 35 | CCGUGCAG CUGAUGA X GAA AGUCCUGC | 175 |
| 302 | CAGGACUUC UGCACGGA | 36 | UCCGUGCA CUGAUGA X GAA AAGUCCUG | 176 |
| 320 | CUGGCCGUC UCCAGUGC | 37 | GCACUGGA CUGAUGA X GAA ACGGCCAG | 177 |
| 322 | GGCCGUCUC CAGUGCCA | 38 | UGGCACUG CUGAUGA X GAA AGACGGCC | 178 |
| 334 | UGCCAACUU CAUUCCCA | 39 | UGGGAAUG CUGAUGA X GAA AGUUGGCA | 179 |
| 335 | GCCAACUUC AUUCCCAC | 40 | GUGGGAAU CUGAUGA X GAA AAGUUGGC | 180 |
| 338 | AACUUCAUU CCCACGGU | 41 | ACCGUGGG CUGAUGA X GAA AUGAAGUU | 181 |
| 339 | ACUUCAUUC CCACGGUC | 42 | GACCGUGG CUGAUGA X GAA AAUGAAGU | 182 |
| 347 | CCCACGGUC ACUGCCAU | 43 | AUGGCAGU CUGAUGA X GAA ACCGUGGG | 183 |
| 356 | ACUGCCAUC UCGACCAG | 44 | CUGGUCGA CUGAUGA X GAA AUGGCAGU | 184 |
| 358 | UGCCAUCUC GACCAGUC | 45 | GACUGGUC CUGAUGA X GAA AGAUGGCA | 185 |
| 366 | CGACCAGUC CGGACCUG | 46 | CAGGUCCG CUGAUGA X GAA ACUGGUCG | 186 |
| 398 | CCCGCCCUC GUCUCCUC | 47 | GAGGAGAC CUGAUGA X GAA AGGGCGGG | 187 |
| 401 | GCCCUCGUC UCCUCUGU | 48 | ACAGGAGA CUGAUGA X GAA ACGAGGGC | 188 |
| 403 | CCUCGUCUC CUCUGUGG | 49 | CCACAGAG CUGAUGA X GAA AGACGAGG | 189 |
| 406 | CGUCUCCUC UGUGGCCC | 50 | GGGCCACA CUGAUGA X GAA AGGAGACG | 190 |
| 418 | GGCCCCAUC GCAGACCA | 51 | UGGUCUGC CUGAUGA X GAA AUGGGGCC | 191 |

TABLE III-continued

Human C-fos Hammerhead Ribozyme and Target Sequences

| nt Position | Target site | SEQ. ID.NOS | Ribozyme Sequence | SEQ. ID.NOS |
|---|---|---|---|---|
| 435 | GAGCCCCUC ACCCUUUC | 52 | GAAAGGGU CUGAUGA X GAA AGGGGCUC | 192 |
| 441 | CUCACCCUU UCGGAGUC | 53 | GACUCCGA CUGAUGA X GAA AGGGUGAG | 193 |
| 442 | UCACCCUUU CGGAGUCC | 54 | GGACUCCG CUGAUGA X GAA AAGGGUGA | 194 |
| 443 | CACCCUUUC GGAGUCCC | 55 | GGGACUCC CUGAUGA X GAA AAAGGGUG | 195 |
| 449 | UUCGGAGUC CCCGCCCC | 56 | GGGGCGGG CUGAUGA X GAA ACUCCGAA | 196 |
| 460 | CGCCCCUC CGCUGGGG | 57 | CCCCAGCG CUGAUGA X GAA AGGGGGCG | 197 |
| 471 | CUGGGGCUU ACUCCAGG | 58 | CCUGGAGU CUGAUGA X GAA AGCCCCAG | 198 |
| 472 | UGGGGCUUA CUCCAGGG | 59 | CCCUGGAG CUGAUGA X GAA AAGCCCCA | 199 |
| 475 | GGCUUACUC CAGGGCUG | 60 | CAGCCCUG CUGAUGA X GAA AGUAAGCC | 200 |
| 488 | GCUGGCGUU GUGAAGAC | 61 | GUCUUCAC CUGAUGA X GAA AGCCCAGC | 201 |
| 524 | CAGAGCAUU GGCAGGAG | 62 | CUCCUGCC CUGAUGA X GAA AUGCUCUG | 202 |
| 550 | GGAACAGUU AUCUCCAG | 63 | CUGGAGAU CUGAUGA X GAA ACUGUUCC | 203 |
| 551 | GAACAGUUA UCUCCAGA | 64 | UCUGGAGA CUGAUGA X GAA AACUGUUC | 204 |
| 553 | ACAGUUAUC UCCAGAAG | 65 | CUUCUGGA CUGAUGA X GAA AUAACUGU | 205 |
| 555 | AGUUAUCUC CAGAAGAA | 66 | UUCUUCUG CUGAUGA X GAA AGAUAACU | 206 |
| 581 | AGGAGAAUC GAAGGGAA | 67 | UCCCUUCG CUGAUGA X GAA AUUCUCCU | 207 |
| 597 | AAAGGAAUA AGAUGGCU | 68 | AGCCAUCU CUGAUGA X GAA AUUCCUUU | 208 |
| 645 | UGACUGAUA CACUCCAA | 69 | UUGGAGUG CUGAUGA X GAA AUCAGUCA | 209 |
| 650 | GAUACACUC CAAGCGGA | 70 | UCCGCUUG CUGAUGA X GAA AGUGUAUC | 210 |
| 671 | GACCAACUA GAAGAUGA | 71 | UCAUCUUC CUGAUGA X GAA AGUUGGUC | 211 |
| 685 | UGAGAAGUC UGCUUUGC | 72 | GCAAAGCA CUGAUGA X GAA ACUUCUCA | 212 |
| 690 | AGUCUGCUU UGCAGACC | 73 | GGUCUGCA CUGAUGA X GAA AGCAGACU | 213 |
| 691 | GUCUGCUUU GCAGACCG | 74 | CGGUCUGC CUGAUGA X GAA AAGCAGAC | 214 |
| 704 | ACCGAGAUU GCCAACCU | 75 | AGGUUGGC CUGAUGA X GAA AUCUCGGU | 215 |
| 734 | GAAAACUA GAGUUCAU | 76 | AUGAACUC CUGAUGA X GAA AGUUUUUC | 216 |
| 739 | ACUAGAGUU CAUCCUGG | 77 | CCAGGAUG CUGAUGA X GAA ACUCUAGU | 271 |
| 740 | CUAGAGUUC AUCCUGGC | 78 | GCCAGGAU CUGAUGA X GAA AACUCUAG | 218 |
| 743 | GAGUUCAUC CUGGCAGC | 79 | GCUGCCAG CUGAUGA X GAA AUGAACUC | 219 |
| 753 | UGGCAGCUC ACCGACCU | 80 | AGGUCGGU CUGAUGA X GAA AGCUGCCA | 220 |
| 773 | UGCAAGAUC CCUGAUGA | 81 | UCAUCAGG CUGAUGA X GAA AUCUUGCA | 221 |
| 790 | CCUGGGCUU CCCAGAAG | 82 | CUUCUGGG CUGAUGA X GAA AGCCCAGG | 222 |
| 791 | CUGGGCUUC CCAGAAGA | 83 | UCUUCUGG CUGAUGA X GAA AAGCCCAG | 223 |
| 805 | AGAGAUGUC UGUGGCUU | 84 | AAGCCACA CUGAUGA X GAA ACAUCUCU | 224 |
| 813 | CUGUGGCUU CCCUUGAU | 85 | AUCAAGGG CUGAUGA X GAA AGCCACAG | 225 |
| 814 | UGUGGCUUC CCUUGAUC | 86 | GAUCAAGG CUGAUGA X GAA AAGCCACA | 226 |
| 818 | GCUUCCCUU GAUCUGAC | 87 | GUCAGAUC CUGAUGA X GAA AGGGAAGC | 227 |
| 822 | CCCUUGAUC UGACUGGG | 88 | CCCAGUCA CUGAUGA X GAA AUCAAGGG | 228 |
| 845 | CCAGAGGUU GCCACCCC | 89 | GGGGUGGC CUGAUGA X GAA ACCUCUGG | 229 |
| 859 | CCCGGAGUC UGAGGAGG | 90 | CCUCCUCA CUGAUGA X GAA ACUCCGGG | 230 |
| 871 | GGAGGCCUU CACCCUGC | 91 | GCAGGGUG CUGAUGA X GAA AGGCCUCC | 231 |
| 872 | GAGGCCUUC ACCCUGCC | 92 | GGCAGGGU CUGAUGA X GAA AAGGCCUC | 232 |
| 882 | CCCUGCCUC UCCUCAAU | 93 | AUUGAGGA CUGAUGA X GAA AGGCAGGG | 233 |
| 884 | CUGCCUCUC CUCAAUGA | 94 | UCAUUGAG CUGAUGA X GAA AGAGGCAG | 234 |
| 887 | CCUCUCCUC AAUGACCC | 95 | GGGUCAUU CUGAUGA X GAA AGGAGAGG | 235 |
| 910 | CAAGCCCUC AGUGGAAC | 96 | GUUCCACU CUGAUGA X GAA AGGGCUUG | 236 |
| 923 | GAACCUGUC AAGAGCAU | 97 | AUGCUCUU CUGAUGA X GAA ACAGGUUC | 237 |
| 932 | AAGAGCAUC AGCAGCAU | 98 | AUGCUGCU CUGAUGA X GAA AUGCUCUU | 238 |
| 961 | CGAGCCCUU UGAUGACU | 99 | AGUCAUCA CUGAUGA X GAA AGGGCUCG | 239 |
| 962 | GAGCCCUUU GAUGACUU | 100 | AAGUCAUC CUGAUGA X GAA AAGGGCUC | 240 |
| 970 | UGAUGACUU CCUGUUCC | 101 | GGAACAGG CUGAUGA X GAA AGUCAUCA | 241 |
| 971 | GAUGACUUC CUGUUCCC | 102 | GGGAACAG CUGAUGA X GAA AAGUCAUC | 242 |
| 976 | CUUCCUGUU CCCAGCAU | 103 | AUGCUGGG CUGAUGA X GAA ACAGGAAG | 243 |
| 977 | UUCCUGUUC CCAGCAUC | 104 | GAUGCUGG CUGAUGA X GAA AACAGGAA | 244 |
| 985 | CCCAGCAUC AUCCAGGC | 105 | GCCUGGAU CUGAUGA X GAA AUGCUGGG | 245 |
| 988 | AGCAUCAUC CAGGCCCA | 106 | UGGGCCUG CUGAUGA X GAA AUGAUGCU | 246 |
| 1003 | CAGUGGCUC UGAGACUG | 107 | CUGUCUCA CUGAUGA X GAA AGCCACUG | 247 |
| 1018 | AGCCCGCUC CGUGCCAG | 108 | CUGGCACG CUGAUGA X GAA AGCGGGCU | 248 |
| 1037 | AUGGACCUA UCUGGGUC | 109 | GACCCAGA CUGAUGA X GAA AGGUCCAU | 249 |
| 1039 | GGACCUAUC UGGGUCCU | 110 | AGGACCCA CUGAUGA X GAA AUAGGUCC | 250 |
| 1045 | AUCUGGGUC CUUCUAUG | 111 | CAUAGAAG CUGAUGA X GAA ACCCAGAU | 251 |
| 1048 | UGGGUCCUU CUAUGCAG | 112 | CUGCAUAG CUGAUGA X GAA AGGACCCA | 252 |
| 1049 | GGGUCCUUC UAUGCAGC | 113 | GCUGCAUA CUGAUGA X GAA AAGGACCC | 253 |
| 1051 | GUCCUUCUA UGCAGCAG | 114 | CUGCUGCA CUGAUGA X GAA AGAAGGAC | 254 |
| 1071 | GGGAGCCUC UGCACAGU | 115 | ACUGUGCA CUGAUGA X GAA AGGCUCCC | 255 |
| 1084 | CAGUGGCUC CCUGGGGA | 116 | UCCCCAGG CUGAUGA X GAA AGCCACUG | 256 |
| 1131 | UGUGCACUC CGGUGGUC | 117 | GACCACCG CUGAUGA X GAA AGUGCACA | 257 |
| 1139 | CCGGUGGUC ACCGUAC | 118 | GUACAGGU CUGAUGA X GAA ACCACCGG | 258 |
| 1146 | UCACCUGUA CUCCCAGC | 119 | GCUGGGAG CUGAUGA X GAA ACAGGUGA | 259 |
| 1149 | CCUGUACUC CCAGCUGC | 120 | GCAGCUGG CUGAUGA X GAA AGUACAGG | 260 |
| 1164 | GCACUGCUU ACACGUCU | 121 | AGACGUGU CUGAUGA X GAA AGCAGUGC | 261 |
| 1165 | CACUGCUUA CACGUCUU | 122 | AAGACGUG CUGAUGA X GAA AAGCAGUG | 262 |
| 1171 | UUACACGUC UUCCUUCG | 123 | CGAAGGAA CUGAUGA X GAA ACGUGUAA | 263 |
| 1173 | ACACGUCUU CCUUCGUC | 124 | GACGAAGG CUGAUGA X GAA AGACGUGU | 264 |
| 1174 | CACGUCUUC CUUCGUCU | 125 | AGACGAAG CUGAUGA X GAA AAGACGUG | 265 |

TABLE III-continued

Human C-fos Hammerhead Ribozyme and Target Sequences

| nt Position | Target site | SEQ. ID.NOS | Ribozyme Sequence | SEQ. ID.NOS |
|---|---|---|---|---|
| 1177 | GUCUUCCUU CGUCUUCA | 126 | UGAAGACG CUGAUGA X GAA AGGAAGAC | 266 |
| 1178 | UCUUCCUUC GUCUUCAC | 127 | GUGAAGAC CUGAUGA X GAA AAGGAAGA | 267 |
| 1181 | UCCUUCGUC UUCACCUA | 128 | UAGGUGAA CUGAUGA X GAA ACGAAGGA | 268 |
| 1183 | CUUCGUCUU CACCUACC | 129 | GGUAGGUG CUGAUGA X GAA AGACGAAG | 269 |
| 1184 | UUCGUCUUC ACCUACCC | 130 | GGGUAGGU CUGAUGA X GAA AAGACGAA | 270 |
| 1189 | CUUCACCUA CCCCGAGG | 131 | CCUCGGGG CUGAUGA X GAA AGGUGAAG | 271 |
| 1204 | GGCUGACUC CUUCCCCA | 132 | UGGGGAAG CUGAUGA X GAA AGUCAGCC | 272 |
| 1207 | UGACUCCUU CCCCAGCU | 133 | AGCUGGGG CUGAUGA X GAA AGGAGUCA | 273 |
| 1208 | GACUCCUUC CCCAGCUG | 134 | CAGCUGGG CUGAUGA X GAA AAGGAGUC | 274 |
| 1257 | AUGAGCCUU CCUCUGAU | 135 | GUCAGAGG CUGAUGA X GAA AGGCUCAU | 275 |
| 1258 | UGAGCCUUC CUCUGACU | 136 | AGUCAGAG CUGAUGA X GAA AAGGCUCA | 276 |
| 1261 | GCCUUCCUC UGACUCGC | 137 | GCGAGUCA CUGAUGA X GAA AGGAAGGC | 277 |
| 1267 | CUCUGACUC GCUCAGCU | 138 | AGCUGAGC CUGAUGA X GAA AGUCAGAG | 278 |
| 1271 | GACUCGCUC AGCUCACC | 139 | GGCGAGCU CUGAUGA X GAA AGCGAGUC | 279 |
| 1276 | GCUCAGCUC ACCCACGC | 140 | GCGUGGGU CUGAUGA X GAA AGCUGAGC | 280 |

Where "X" represents stem II region of a HH ribozyme (Hertel et al., 1992 Nucleic Acids Res. 20 3252). The length of stem II may be ≧ 2 base-pairs.

TABLE IV

TABLE IV:Human C-fos Hairpin Ribozyme and Target Sequence

| nt. Position | Ribozymen Sequence | SEQ.ID. NOS. | Target Sequence | SEQ.ID. NOS. |
|---|---|---|---|---|
| 46 | CGCCGC AGAA GCCG ACCAGAGAAACACACGUUGUGGUACAUUACCUGGUA | 281 | CGGCG GCC GCGGCG | 325 |
| 87 | AAGCAG AGAA GGGU ACCAGAGAAACACACGUUGUGGUACAUUACCUGGUA | 282 | ACCCA GCU CUGCUU | 326 |
| 92 | CUGUGA AGAA GAGC ACCAGAGAAACACACGUUGUGGUACAUUACCUGGUA | 283 | GCUCU GCU UCACAG | 327 |
| 110 | GGCGGA AGAA GUG ACCAGAGAAACACACGUUGUGGUACAUUACCUGGUA | 284 | CACCU GUC UCCGCC | 328 |
| 116 | CCGAGG AGAA GAGA ACCAGAGAAACACACGUUGUGGUACAUUACCUGGUA | 285 | UCUCC GCC CCUCGG | 329 |
| 124 | GCGAGG AGAA GAGG ACCAGAGAAACACACGUUGUGGUACAUUACCUGGUA | 286 | CCUCG GCC CCUCGC | 330 |
| 136 | AGGCAA AGAA GGGC ACCAGAGAAACACACGUUGUGGUACAUUACCUGGUA | 287 | GCCCG GCU UUGCCU | 331 |
| 179 | CUCGUA AGAA GCGU ACCAGAGAAACACACGUUGUGGUACAUUACCUGGUA | 288 | ACGCA GAC UACGAG | 332 |
| 201 | UGCUGC AGAA GGAG ACCAGAGAAACACACGUUGUGGUACAUUACCUGGUA | 289 | CUCCC GCU GCAGCA | 333 |
| 221 | AUCCCC AGAA GGGG ACCAGAGAAACACACGUUGUGGUACAUUACCUGGUA | 290 | CCCCG GCC GGGGAU | 334 |
| 257 | GAAGGA AGAA GCGG ACCAGAGAAACACACGUUGUGGUACAUUACCUGGUA | 291 | CCGCA GAC UCCUUC | 335 |
| 308 | GGCCAG AGAA GUGC ACCAGAGAAACACACGUUGUGGUACAUUACCUGGUA | 292 | GCACG GAC CUGGCC | 336 |
| 317 | ACUGGA AGAA GCCA ACCAGAGAAACACACGUUGUGGUACAUUACCUGGUA | 293 | UGGCC GUC UCCAGU | 338 |
| 363 | GGUCCG AGAA GGUC ACCAGAGAAACACACGUUGUGGUACAUUACCUGGUA | 294 | GACCA GUC CGGACC | 338 |
| 368 | CUGCAG AGAA GGAC ACCAGAGAAACACACGUUGUGGUACAUUACCUGGUA | 295 | GUCCG GAC CUGCAG | 339 |
| 388 | AGGGCG AGAA GCAC ACCAGAGAAACACACGUUGUGGUACAUUACCUGGUA | 296 | GUGCA GCC CGCCCU | 340 |
| 392 | GACGAG AGAA GGCU ACCAGAGAAACACACGUUGUGGUACAUUACCUGGUA | 297 | AGCCC GCC CUCGUC | 341 |
| 421 | GCUCUG AGAA GCGA ACCAGAGAAACACACGUUGUGGUACAUUACCUGGUA | 298 | UCGCA GAC CAGAGC | 342 |
| 452 | GGAGGG AGAA GGGA ACCAGAGAAACACACGUUGUGGUACAUUACCUGGUA | 299 | UCCCC GCC CCCUCC | 343 |
| 461 | AGCCCC AGAA GAGG ACCAGAGAAACACACGUUGUGGUACAUUACCUGGUA | 300 | CCUCC GCU GGGGCU | 344 |
| 637 | GUAUCA AGAA GCUC ACCAGAGAAACACACGUUGUGGUACAUUACCUGGUA | 301 | GAGCU GAC UGAUAC | 345 |
| 662 | UAGUUG AGAA GUCU ACCAGAGAAACACACGUUGUGGUACAUUACCUGGUA | 302 | AGACA GAC CAACUA | 346 |
| 686 | CUGCAA AGAA GACU ACCAGAGAAACACACGUUGUGGUACAUUACCUGGUA | 303 | AGUCU GCU UUGCAG | 347 |
| 694 | AUCUCG AGAA GCAA ACCAGAGAAACACACGUUGUGGUACAUUACCUGGUA | 304 | UUGCA GAC CGAGAU | 348 |
| 712 | UCCUUC AGAA GGUU ACCAGAGAAACACACGUUGUGGUACAUUACCUGGUA | 305 | AACCU GCU GAAGGA | 349 |
| 749 | UCGGUG AGAA GCCA ACCAGAGAAACACACGUUGUGGUACAUUACCUGGUA | 306 | UGGCA GCU CACCGA | 350 |
| 756 | AGGCAG AGAA GUGA ACCAGAGAAACACACGUUGUGGUACAUUACCUGGUA | 307 | UCACC GAC CUGCCU | 351 |
| 761 | CUUGCA AGAA GGUC ACCAGAGAAACACACGUUGUGGUACAUUACCUGGUA | 308 | GACCU GCC UGCAAG | 352 |
| 776 | CAGGUC AGAA GGGA ACCAGAGAAACACACGUUGUGGUACAUUACCUGGUA | 309 | UCCCU GAU GACCUG | 353 |
| 823 | CCCCCA AGAA GAUC ACCAGAGAAACACACGUUGUGGUACAUUACCUGGUA | 310 | GAUCU GAC UGGGGG | 354 |
| 877 | AGGAGA AGAA GGGU ACCAGAGAAACACACGUUGUGGUACAUUACCUGGUA | 311 | ACCCU GCC UCUCCU | 355 |
| 312 | GCUGGG AGAA GGAA ACCAGAGAAACACACGUUGUGGUACAUUACCUGGUA | 312 | UUCCU GUU CCCAGC | 356 |
| 1010 | GGAGCG AGAA GUCU ACCAGAGAAACACACGUUGUGGUACAUUACCUGGUA | 313 | AGACA GCC CGCUCC | 357 |
| 1014 | GCACGG AGAA GGCU ACCAGAGAAACACACGUUGUGGUACAUUACCUGGUA | 314 | AGCCC GCU CCGUGC | 358 |
| 1058 | CUCCCA AGAA GCUG ACCAGAGAAACACACGUUGUGGUACAUUACCUGGUA | 315 | CAGCA GAC UGGGAG | 359 |
| 1152 | CAGUGC AGAA GGGA ACCAGAGAAACACACGUUGUGGUACAUUACCUGGUA | 316 | UCCCA GCU GCACUG | 360 |
| 1160 | CGUGUA AGAA GUGC ACCAGAGAAACACACGUUGUGGUACAUUACCUGGUA | 317 | GCACU GCU UACACG | 361 |
| 1199 | GAAGGA AGAA GCCU ACCAGAGAAACACACGUUGUGGUACAUUACCUGGUA | 318 | AGGCU GAC UCCUUC | 362 |
| 1212 | CUGCAC AGAA GGGG ACCAGAGAAACACACGUUGUGGUACAUUACCUGGUA | 319 | CCCCA GCU GUGCAG | 363 |
| 1220 | GUGGGC AGAA GCAC ACCAGAGAAACACACGUUGUGGUACAUUACCUGGUA | 320 | GUGCA GCU GCCCAC | 364 |
| 1223 | GCGGUG AGAA GCUG ACCAGAGAAACACACGUUGUGGUACAUUACCUGGUA | 321 | CAGCU GCC CACCGC | 365 |
| 1262 | GAGCGA AGAA GGCA ACCAGAGAAACACACGUUGUGGUACAUUACCUGGUA | 322 | CCUCU GCU UCGCUC | 366 |
| 1272 | UGGGUG AGAA GAGC ACCAGAGAAACACACGUUGUGGUACAUUACCUGGUA | 323 | GCUCA GCU CACCCA | 367 |
| 1285 | AGGGCC AGAA GCGU ACCAGAGAAACACACGUUGUGGUACAUUACCUGGUA | 324 | ACGCU GCU GGCCCU | 368 |

TABLE V

C-fos Ribozyme-Mediated Inhibition of Stromelysin Gene Expression In Vivo

| Ribozymes | Percent Inhibition |
|---|---|
| 268 Amino Ribozyme (Exp. 1) | 47 ± 10% |
| 268 Amino Ribozyme (Exp. 2) | 40 ± 6% |

What is claimed is:

1. An enzymatic nucleic acid molecule which specifically cleaves RNA encoded by a c-fos gene, wherein said enzymatic nucleic acid molecule is in a hairpin motif.

2. An enzymatic nucleic acid molecule which specifically cleaves RNA encoded by a c-fos gene, wherein said enzymatic nucleic acid molecule is in a hammerhead motif, wherein the binding arms of said enzymatic nucleic acid molecule comprise sequences complementary to any of sequences defined as SEQ. ID. NOS. 1–140.

3. The enzymatic nucleic acid molecule of claim 2, wherein said enzymatic nucleic acid molecule comprises a stem II region of length greater than or equal to 2 base pairs.

4. The enzymatic nucleic acid molecule of claim 1, wherein said hairpin motif consists essentially of any sequence selected from the sequences defined as SEQ. ID. NOS. 281–324.

5. The enzymatic nucleic acid molecule of claim 1, wherein the binding arms of said enzymatic nucleic acid molecule comprise sequences complementary to any of sequences defined as SEQ. ID. NOS. 325–368.

6. An enzymatic nucleic acid molecule which specifically cleaves RNA encoded by a c-fos gene, wherein said enzymatic nucleic acid molecule is in a hepatitis delta virus, VS nucleic acid, group I intron, Group II intron, or RNase P nucleic acid motif.

7. The enzymatic nucleic acid molecule of any of claims 1, 2, or 6, wherein said nucleic acid comprises between 12 and 100 bases complementary to said RNA.

8. The enzymatic nucleic acid molecule of any of claims 1, 2, or 6, wherein said enzymatic nucleic acid molecule comprises between 14 and 24 bases complementary to said RNA encoded by the c-fos gene.

9. The enzymatic nucleic acid molecule of claim 2, wherein said hammerhead motif consists essentially of any sequence selected from the sequences defined as SEQ. ID NOS. 141–280.

10. A mammalian cell including an enzymatic nucleic acid molecule of any one of any of claims 1, 2, or 6, wherein said mammalina cell is not a living human.

11. The mammallian cell of claim 10, wherein said cell is a human cell.

12. An expression vector comprising nucleic acid sequence encoding at least one of the enzymatic nucleic acid molecule of any of claims 1, 2, or 6, in a manner which allows expression of that enzymatic nucleic acid molecule.

13. A mammalian cell including an expression vector of claim 12, wherein said mammalian cell is not a living human.

14. The mammalian cell of claim 13, wherein said mammalian cell is a human cell.

15. The enzymatic nucleic acid molecule of claim 2, wherein said enzymatic nucleic acid molecule comprises: at least five ribose residues; phosphorothioate linkages on at least three of the 5' terminal nucleotides; a 2'-C-allyl modification at position No. 4 of said enzymatic nucleic acid; at least ten 2'-O-methyl modifications; and a 3'-end modification.

16. The enzymatic nucleic acid molecule of claim 15, wherein said 3'-end modification is a 3'-3'linked inverted deoxyribose moiety.

17. The enzymatic nucleic acid molecule of claim 2, wherein said enzymatic nucleic acid molecule comprises: at least five ribose residues; phosphorothioate linkages on at least three of the 5' terminal nucleotides; a 2'-amino modification at position No. 4, or at position No. 7 or at position No. 4 and position No. 7 of said enzymatic nucleic acid molecule; at least ten 2'-O-methyl modifications; and a 3'-end modification.

18. The enzymatic nucleic acid molecule of claim 2, wherein said enzymatic nucleic acid molecule comprises: at least five ribose residues; phosphorothioate linkages on at least three of the 5' terminal nucleotides; an abasic substitution position No. 4, or at position No. 7 or at position No. 4 and position No. 7 of said enzymatic nucleic acid molecule; at least ten 2'-O-methyl modifications; and a 3'-end modification.

19. The enzymatic nucleic acid molecule of claim 2, wherein said enzymatic nucleic acid molecule comprises: at least five ribose residues; phosphorothioate linkages on at least three of the 5' terminal nucleotides; a 6-methyl uridine substitution at position No. 4, or at position No. 7 or at position No. 4 and position No. 7 of said enzymatic nucleic acid molecule; at least ten 2'-O-methyl modifications; and a 3'-end modification.

* * * * *

SEQUENCE LISTING

<160> NUMBER OF SEQ ID NOS: 375

<210> SEQ ID NO 1
<211> LENGTH: 17
<212> TYPE: RNA
<213> ORGANISM: Homo sapiens

<400> SEQUENCE: 1
aaccgcaucu gcagcga                                                   17

<210> SEQ ID NO 2
<211> LENGTH: 17
<212> TYPE: RNA
<213> ORGANISM: Homo sapiens

<400> SEQUENCE: 2
accgugcucc uacccag                                                   17

<210> SEQ ID NO 3
<211> LENGTH: 17
<212> TYPE: RNA
<213> ORGANISM: Homo sapiens

<400> SEQUENCE: 3
gugcuccuac ccagcuc                                                   17

<210> SEQ ID NO 4
<211> LENGTH: 17
<212> TYPE: RNA
<213> ORGANISM: Homo sapiens

<400> SEQUENCE: 4
acccagcucu gcuucac                                                   17

<210> SEQ ID NO 5
<211> LENGTH: 17
<212> TYPE: RNA
<213> ORGANISM: Homo sapiens

<400> SEQUENCE: 5
gcucugcuuc acagcgc                                                   17

<210> SEQ ID NO 6
<211> LENGTH: 17
<212> TYPE: RNA
<213> ORGANISM: Homo sapiens

<400> SEQUENCE: 6

-continued cucugcuuca cagcgcc 17

<210> SEQ ID NO 7
<211> LENGTH: 17
<212> TYPE: RNA
<213> ORGANISM: Homo sapiens

<400> SEQUENCE: 7
ccaccugucu ccgcccc 17

<210> SEQ ID NO 8
<211> LENGTH: 17
<212> TYPE: RNA
<213> ORGANISM: Homo sapiens

<400> SEQUENCE: 8
accugucucc gcccuc 17

<210> SEQ ID NO 9
<211> LENGTH: 17
<212> TYPE: RNA
<213> ORGANISM: Homo sapiens

<400> SEQUENCE: 9 ccgcccucg gccccuc 17

<210> SEQ ID NO 10
<211> LENGTH: 17
<212> TYPE: RNA
<213> ORGANISM: Homo sapiens

<400> SEQUENCE: 10 cggcccucg cccggcu 17

<210> SEQ ID NO 11
<211> LENGTH: 17
<212> TYPE: RNA
<213> ORGANISM: Homo sapiens

<400> SEQUENCE: 11
gcccggcuuu gccuaac 17

<210> SEQ ID NO 12
<211> LENGTH: 17
<212> TYPE: RNA
<213> ORGANISM: Homo sapiens

<400> SEQUENCE: 12
cccggcuuug ccuaacc 17

<210> SEQ ID NO 13
<211> LENGTH: 17
<212> TYPE: RNA
<213> ORGANISM: Homo sapiens

<400> SEQUENCE: 13
cuuugccuaa ccgccac 17

<210> SEQ ID NO 14
<211> LENGTH: 17
<212> TYPE: RNA
<213> ORGANISM: Homo sapiens -continued

```
<400> SEQUENCE: 14
gaugauguuc ucgggcu                                              17

<210> SEQ ID NO 15
<211> LENGTH: 17
<212> TYPE: RNA
<213> ORGANISM: Homo sapiens

<400> SEQUENCE: 15
augauguucu cgggcuu                                              17

<210> SEQ ID NO 16
<211> LENGTH: 17
<212> TYPE: RNA
<213> ORGANISM: Homo sapiens

<400> SEQUENCE: 16
cucgggcuuc aacgcag                                              17

<210> SEQ ID NO 17
<211> LENGTH: 17
<212> TYPE: RNA
<213> ORGANISM: Homo sapiens

<400> SEQUENCE: 17
ucgggcuuca acgcaga                                              17

<210> SEQ ID NO 18
<211> LENGTH: 17
<212> TYPE: RNA
<213> ORGANISM: Homo sapiens

<400> SEQUENCE: 18
cgcagacuac gaggcgu                                              17

<210> SEQ ID NO 19
<211> LENGTH: 17
<212> TYPE: RNA
<213> ORGANISM: Homo sapiens

<400> SEQUENCE: 19
ggcgucaucc ucccgcu                                              17

<210> SEQ ID NO 20
<211> LENGTH: 17
<212> TYPE: RNA
<213> ORGANISM: Homo sapiens

<400> SEQUENCE: 20
gucauccucc cgcugca                                              17

<210> SEQ ID NO 21
<211> LENGTH: 17
<212> TYPE: RNA
<213> ORGANISM: Homo sapiens

<400> SEQUENCE: 21
cagcgcgucc ccggccg                                              17

<210> SEQ ID NO 22
<211> LENGTH: 17
<212> TYPE: RNA
<213> ORGANISM: Homo sapiens
```

```
<400> SEQUENCE: 22
ccggggauag ccucucu                                              17

<210> SEQ ID NO 23
<211> LENGTH: 17
<212> TYPE: RNA
<213> ORGANISM: Homo sapiens

<400> SEQUENCE: 23
gauagccucu cuuacua                                              17

<210> SEQ ID NO 24
<211> LENGTH: 17
<212> TYPE: RNA
<213> ORGANISM: Homo sapiens

<400> SEQUENCE: 24
uagccucucu uacuacc                                              17

<210> SEQ ID NO 25
<211> LENGTH: 17
<212> TYPE: RNA
<213> ORGANISM: Homo sapiens

<400> SEQUENCE: 25
gccucucuua cuaccac                                              17

<210> SEQ ID NO 26
<211> LENGTH: 17
<212> TYPE: RNA
<213> ORGANISM: Homo sapiens

<400> SEQUENCE: 26
ccucucuuac uaccacu                                              17

<210> SEQ ID NO 27
<211> LENGTH: 17
<212> TYPE: RNA
<213> ORGANISM: Homo sapiens

<400> SEQUENCE: 27
cucuuacuac cacucac                                              17

<210> SEQ ID NO 28
<211> LENGTH: 17
<212> TYPE: RNA
<213> ORGANISM: Homo sapiens

<400> SEQUENCE: 28
cuaccacuca cccgcag                                              17

<210> SEQ ID NO 29
<211> LENGTH: 17
<212> TYPE: RNA
<213> ORGANISM: Homo sapiens

<400> SEQUENCE: 29
cgcagacucc uucucca                                              17

<210> SEQ ID NO 30
<211> LENGTH: 17
<212> TYPE: RNA
```

<213> ORGANISM: Homo sapiens

<400> SEQUENCE: 30
agacuccuuc uccagca                                           17

<210> SEQ ID NO 31
<211> LENGTH: 17
<212> TYPE: RNA
<213> ORGANISM: Homo sapiens

<400> SEQUENCE: 31
gacuccuucu ccagcau                                           17

<210> SEQ ID NO 32
<211> LENGTH: 17
<212> TYPE: RNA
<213> ORGANISM: Homo sapiens

<400> SEQUENCE: 32
cuccuucucc agcaugg                                           17

<210> SEQ ID NO 33
<211> LENGTH: 17
<212> TYPE: RNA
<213> ORGANISM: Homo sapiens

<400> SEQUENCE: 33
caugggcucg ccuguca                                           17

<210> SEQ ID NO 34
<211> LENGTH: 17
<212> TYPE: RNA
<213> ORGANISM: Homo sapiens

<400> SEQUENCE: 34
ucgccuguca acgcgca                                           17

<210> SEQ ID NO 35
<211> LENGTH: 17
<212> TYPE: RNA
<213> ORGANISM: Homo sapiens

<400> SEQUENCE: 35
gcaggacuuc ugcacgg                                           17

<210> SEQ ID NO 36
<211> LENGTH: 17
<212> TYPE: RNA
<213> ORGANISM: Homo sapiens

<400> SEQUENCE: 36
caggacuucu gcacgga                                           17

<210> SEQ ID NO 37
<211> LENGTH: 17
<212> TYPE: RNA
<213> ORGANISM: Homo sapiens

<400> SEQUENCE: 37
cuggccgucu ccagugc                                           17

<210> SEQ ID NO 38
<211> LENGTH: 17

```
<212> TYPE: RNA
<213> ORGANISM: Homo sapiens

<400> SEQUENCE: 38
ggccgucucc agugcca                                                   17

<210> SEQ ID NO 39
<211> LENGTH: 17
<212> TYPE: RNA
<213> ORGANISM: Homo sapiens

<400> SEQUENCE: 39
ugccaacuuc auuccca                                                   17

<210> SEQ ID NO 40
<211> LENGTH: 17
<212> TYPE: RNA
<213> ORGANISM: Homo sapiens

<400> SEQUENCE: 40
gccaacuuca uucccac                                                   17

<210> SEQ ID NO 41
<211> LENGTH: 17
<212> TYPE: RNA
<213> ORGANISM: Homo sapiens

<400> SEQUENCE: 41
aacuucauuc ccacggu                                                   17

<210> SEQ ID NO 42
<211> LENGTH: 17
<212> TYPE: RNA
<213> ORGANISM: Homo sapiens

<400> SEQUENCE: 42
acuucauucc cacguc                                                    17

<210> SEQ ID NO 43
<211> LENGTH: 17
<212> TYPE: RNA
<213> ORGANISM: Homo sapiens

<400> SEQUENCE: 43
cccacgguca cugccau                                                   17

<210> SEQ ID NO 44
<211> LENGTH: 17
<212> TYPE: RNA
<213> ORGANISM: Homo sapiens

<400> SEQUENCE: 44
acugccaucu cgaccag                                                   17

<210> SEQ ID NO 45
<211> LENGTH: 17
<212> TYPE: RNA
<213> ORGANISM: Homo sapiens

<400> SEQUENCE: 45
ugccaucucg accaguc                                                   17

<210> SEQ ID NO 46
```

<211> LENGTH: 17
<212> TYPE: RNA
<213> ORGANISM: Homo sapiens

<400> SEQUENCE: 46
cgaccagucc ggaccug                                                    17

<210> SEQ ID NO 47
<211> LENGTH: 17
<212> TYPE: RNA
<213> ORGANISM: Homo sapiens

<400> SEQUENCE: 47
cccgcccucg ucuccuc                                                    17

<210> SEQ ID NO 48
<211> LENGTH: 17
<212> TYPE: RNA
<213> ORGANISM: Homo sapiens

<400> SEQUENCE: 48
gcccucgucu ccucugu                                                    17

<210> SEQ ID NO 49
<211> LENGTH: 17
<212> TYPE: RNA
<213> ORGANISM: Homo sapiens

<400> SEQUENCE: 49
ccucgucucc ucugugg                                                    17

<210> SEQ ID NO 50
<211> LENGTH: 17
<212> TYPE: RNA
<213> ORGANISM: Homo sapiens

<400> SEQUENCE: 50 cgucccucu guggccc                                                     17

<210> SEQ ID NO 51
<211> LENGTH: 17
<212> TYPE: RNA
<213> ORGANISM: Homo sapiens

<400> SEQUENCE: 51
ggccccaucg cagacca                                                    17

<210> SEQ ID NO 52
<211> LENGTH: 17
<212> TYPE: RNA
<213> ORGANISM: Homo sapiens

<400> SEQUENCE: 52 gagcccuca cccuuuc                                                     17

<210> SEQ ID NO 53
<211> LENGTH: 17
<212> TYPE: RNA
<213> ORGANISM: Homo sapiens

<400> SEQUENCE: 53
cucacccuuu cggaguc                                                    17

```
<210> SEQ ID NO 54
<211> LENGTH: 17
<212> TYPE: RNA
<213> ORGANISM: Homo sapiens

<400> SEQUENCE: 54
ucacccuuuc ggagucc                                               17

<210> SEQ ID NO 55
<211> LENGTH: 17
<212> TYPE: RNA
<213> ORGANISM: Homo sapiens

<400> SEQUENCE: 55
cacccuuucg gagucccc                                              17

<210> SEQ ID NO 56
<211> LENGTH: 17
<212> TYPE: RNA
<213> ORGANISM: Homo sapiens

<400> SEQUENCE: 56
uucggagucc ccgcccc                                               17

<210> SEQ ID NO 57
<211> LENGTH: 17
<212> TYPE: RNA
<213> ORGANISM: Homo sapiens

<400> SEQUENCE: 57
cgcccccucc gcugggg                                               17

<210> SEQ ID NO 58
<211> LENGTH: 17
<212> TYPE: RNA
<213> ORGANISM: Homo sapiens

<400> SEQUENCE: 58 cugggggcuua cuccagg                                              17

<210> SEQ ID NO 59
<211> LENGTH: 17
<212> TYPE: RNA
<213> ORGANISM: Homo sapiens

<400> SEQUENCE: 59 ugggcuuac uccaggg                                                17

<210> SEQ ID NO 60
<211> LENGTH: 17
<212> TYPE: RNA
<213> ORGANISM: Homo sapiens

<400> SEQUENCE: 60
ggcuuacucc agggcug                                               17

<210> SEQ ID NO 61
<211> LENGTH: 17
<212> TYPE: RNA
<213> ORGANISM: Homo sapiens

<400> SEQUENCE: 61
gcuggcguug ugaagac                                               17
```

```
<210> SEQ ID NO 62
<211> LENGTH: 17
<212> TYPE: RNA
<213> ORGANISM: Homo sapiens

<400> SEQUENCE: 62
cagagcauug gcaggag                                                17

<210> SEQ ID NO 63
<211> LENGTH: 17
<212> TYPE: RNA
<213> ORGANISM: Homo sapiens

<400> SEQUENCE: 63
ggaacaguua ucuccag                                                17

<210> SEQ ID NO 64
<211> LENGTH: 17
<212> TYPE: RNA
<213> ORGANISM: Homo sapiens

<400> SEQUENCE: 64
gaacaguuau cuccaga                                                17

<210> SEQ ID NO 65
<211> LENGTH: 17
<212> TYPE: RNA
<213> ORGANISM: Homo sapiens

<400> SEQUENCE: 65
acaguuaucu ccagaag                                                17

<210> SEQ ID NO 66
<211> LENGTH: 17
<212> TYPE: RNA
<213> ORGANISM: Homo sapiens

<400> SEQUENCE: 66
aguuaucucc agaagaa                                                17

<210> SEQ ID NO 67
<211> LENGTH: 17
<212> TYPE: RNA
<213> ORGANISM: Homo sapiens

<400> SEQUENCE: 67
aggagaaucc gaaggga                                                17

<210> SEQ ID NO 68
<211> LENGTH: 17
<212> TYPE: RNA
<213> ORGANISM: Homo sapiens

<400> SEQUENCE: 68
aaaggaauaa gauggcu                                                17

<210> SEQ ID NO 69
<211> LENGTH: 17
<212> TYPE: RNA
<213> ORGANISM: Homo sapiens

<400> SEQUENCE: 69
ugacugauac acuccaa                                                17
```

-continued

```
<210> SEQ ID NO 70
<211> LENGTH: 17
<212> TYPE: RNA
<213> ORGANISM: Homo sapiens

<400> SEQUENCE: 70
gauacacucc aagcgga                                                    17

<210> SEQ ID NO 71
<211> LENGTH: 17
<212> TYPE: RNA
<213> ORGANISM: Homo sapiens

<400> SEQUENCE: 71
gaccaacuag aagauga                                                    17

<210> SEQ ID NO 72
<211> LENGTH: 17
<212> TYPE: RNA
<213> ORGANISM: Homo sapiens

<400> SEQUENCE: 72
ugagaagucu gcuuugc                                                    17

<210> SEQ ID NO 73
<211> LENGTH: 17
<212> TYPE: RNA
<213> ORGANISM: Homo sapiens

<400> SEQUENCE: 73
agucugcuuu gcagacc                                                    17

<210> SEQ ID NO 74
<211> LENGTH: 17
<212> TYPE: RNA
<213> ORGANISM: Homo sapiens

<400> SEQUENCE: 74
gucugcuuug cagaccg                                                    17

<210> SEQ ID NO 75
<211> LENGTH: 17
<212> TYPE: RNA
<213> ORGANISM: Homo sapiens

<400> SEQUENCE: 75
accgagauug ccaaccu                                                    17

<210> SEQ ID NO 76
<211> LENGTH: 17
<212> TYPE: RNA
<213> ORGANISM: Homo sapiens

<400> SEQUENCE: 76
gaaaaacuag aguucau                                                    17

<210> SEQ ID NO 77
<211> LENGTH: 17
<212> TYPE: RNA
<213> ORGANISM: Homo sapiens

<400> SEQUENCE: 77
```

-continued acuagaguuc auccugg                                              17

<210> SEQ ID NO 78
<211> LENGTH: 17
<212> TYPE: RNA
<213> ORGANISM: Homo sapiens

<400> SEQUENCE: 78
cuagaguuca uccuggc                                              17

<210> SEQ ID NO 79
<211> LENGTH: 17
<212> TYPE: RNA
<213> ORGANISM: Homo sapiens

<400> SEQUENCE: 79
gaguucaucc uggcagc                                              17

<210> SEQ ID NO 80
<211> LENGTH: 17
<212> TYPE: RNA
<213> ORGANISM: Homo sapiens

<400> SEQUENCE: 80
uggcagcuca ccgaccu                                              17

<210> SEQ ID NO 81
<211> LENGTH: 17
<212> TYPE: RNA
<213> ORGANISM: Homo sapiens

<400> SEQUENCE: 81
ugcaagaucc cugauga                                              17

<210> SEQ ID NO 82
<211> LENGTH: 17
<212> TYPE: RNA
<213> ORGANISM: Homo sapiens

<400> SEQUENCE: 82
ccugggcuuc ccagaag                                              17

<210> SEQ ID NO 83
<211> LENGTH: 17
<212> TYPE: RNA
<213> ORGANISM: Homo sapiens

<400> SEQUENCE: 83
cugggcuucc cagaaga                                              17

<210> SEQ ID NO 84
<211> LENGTH: 17
<212> TYPE: RNA
<213> ORGANISM: Homo sapiens

<400> SEQUENCE: 84
agagaugucu guggcuu                                              17

<210> SEQ ID NO 85
<211> LENGTH: 17
<212> TYPE: RNA
<213> ORGANISM: Homo sapiens

<400> SEQUENCE: 85

-continued cuguggcuuc ccuugau                               17

<210> SEQ ID NO 86
<211> LENGTH: 17
<212> TYPE: RNA
<213> ORGANISM: Homo sapiens

<400> SEQUENCE: 86
uguggcuucc cuugauc                               17

<210> SEQ ID NO 87
<211> LENGTH: 17
<212> TYPE: RNA
<213> ORGANISM: Homo sapiens

<400> SEQUENCE: 87
gcuucccuug aucugac                               17

<210> SEQ ID NO 88
<211> LENGTH: 17
<212> TYPE: RNA
<213> ORGANISM: Homo sapiens

<400> SEQUENCE: 88
cccuugaucu gacuggg                               17

<210> SEQ ID NO 89
<211> LENGTH: 17
<212> TYPE: RNA
<213> ORGANISM: Homo sapiens

<400> SEQUENCE: 89
ccagagguug ccacccc                               17

<210> SEQ ID NO 90
<211> LENGTH: 17
<212> TYPE: RNA
<213> ORGANISM: Homo sapiens

<400> SEQUENCE: 90
cccggagucu gaggagg                               17

<210> SEQ ID NO 91
<211> LENGTH: 17
<212> TYPE: RNA
<213> ORGANISM: Homo sapiens

<400> SEQUENCE: 91
ggaggccuuc acccugc                               17

<210> SEQ ID NO 92
<211> LENGTH: 17
<212> TYPE: RNA
<213> ORGANISM: Homo sapiens

<400> SEQUENCE: 92
gaggccuuca cccugcc                               17

<210> SEQ ID NO 93
<211> LENGTH: 17
<212> TYPE: RNA
<213> ORGANISM: Homo sapiens -continued

```
<210> SEQ ID NO 94
<211> LENGTH: 17
<212> TYPE: RNA
<213> ORGANISM: Homo sapiens

<400> SEQUENCE: 93
cccugccucu ccucaau                                              17

<210> SEQ ID NO 94
<211> LENGTH: 17
<212> TYPE: RNA
<213> ORGANISM: Homo sapiens

<400> SEQUENCE: 94
cugccucucc ucaauga                                              17

<210> SEQ ID NO 95
<211> LENGTH: 17
<212> TYPE: RNA
<213> ORGANISM: Homo sapiens

<400> SEQUENCE: 95
ccucuccuca augaccc                                              17

<210> SEQ ID NO 96
<211> LENGTH: 17
<212> TYPE: RNA
<213> ORGANISM: Homo sapiens

<400> SEQUENCE: 96
caagcccuca guggaac                                              17

<210> SEQ ID NO 97
<211> LENGTH: 17
<212> TYPE: RNA
<213> ORGANISM: Homo sapiens

<400> SEQUENCE: 97
gaaccuguca agagcau                                              17

<210> SEQ ID NO 98
<211> LENGTH: 17
<212> TYPE: RNA
<213> ORGANISM: Homo sapiens

<400> SEQUENCE: 98
aagagcauca gcagcau                                              17

<210> SEQ ID NO 99
<211> LENGTH: 17
<212> TYPE: RNA
<213> ORGANISM: Homo sapiens

<400> SEQUENCE: 99
cgagcccuuu gaugacu                                              17

<210> SEQ ID NO 100
<211> LENGTH: 17
<212> TYPE: RNA
<213> ORGANISM: Homo sapiens

<400> SEQUENCE: 100
gagcccuuug augacuu                                              17

<210> SEQ ID NO 101
<211> LENGTH: 17
<212> TYPE: RNA
<213> ORGANISM: Homo sapiens
```

```
<400> SEQUENCE: 101
ugaugacuuc cuguucc                                          17

<210> SEQ ID NO 102
<211> LENGTH: 17
<212> TYPE: RNA
<213> ORGANISM: Homo sapiens

<400> SEQUENCE: 102
gaugacuucc uguuccc                                          17

<210> SEQ ID NO 103
<211> LENGTH: 17
<212> TYPE: RNA
<213> ORGANISM: Homo sapiens

<400> SEQUENCE: 103
cuuccuguuc ccagcau                                          17

<210> SEQ ID NO 104
<211> LENGTH: 17
<212> TYPE: RNA
<213> ORGANISM: Homo sapiens

<400> SEQUENCE: 104
uuccuguucc cagcauc                                          17

<210> SEQ ID NO 105
<211> LENGTH: 17
<212> TYPE: RNA
<213> ORGANISM: Homo sapiens

<400> SEQUENCE: 105
cccagcauca uccaggc                                          17

<210> SEQ ID NO 106
<211> LENGTH: 17
<212> TYPE: RNA
<213> ORGANISM: Homo sapiens

<400> SEQUENCE: 106
agcaucaucc aggccca                                          17

<210> SEQ ID NO 107
<211> LENGTH: 17
<212> TYPE: RNA
<213> ORGANISM: Homo sapiens

<400> SEQUENCE: 107
caguggcucu gagacag                                          17

<210> SEQ ID NO 108
<211> LENGTH: 17
<212> TYPE: RNA
<213> ORGANISM: Homo sapiens

<400> SEQUENCE: 108
agcccgcucc gugccag                                          17

<210> SEQ ID NO 109
<211> LENGTH: 17
<212> TYPE: RNA
```

-continued

<213> ORGANISM: Homo sapiens

<400> SEQUENCE: 109
auggaccuau cuggguc                                               17

<210> SEQ ID NO 110
<211> LENGTH: 17
<212> TYPE: RNA
<213> ORGANISM: Homo sapiens

<400> SEQUENCE: 110
ggaccuaucu ggguccu                                               17

<210> SEQ ID NO 111
<211> LENGTH: 17
<212> TYPE: RNA
<213> ORGANISM: Homo sapiens

<400> SEQUENCE: 111
aucugggucc uucuaug                                               17

<210> SEQ ID NO 112
<211> LENGTH: 17
<212> TYPE: RNA
<213> ORGANISM: Homo sapiens

<400> SEQUENCE: 112
uggguccuuc uaugcag                                               17

<210> SEQ ID NO 113
<211> LENGTH: 17
<212> TYPE: RNA
<213> ORGANISM: Homo sapiens

<400> SEQUENCE: 113
ggguccuucu augcagc                                               17

<210> SEQ ID NO 114
<211> LENGTH: 17
<212> TYPE: RNA
<213> ORGANISM: Homo sapiens

<400> SEQUENCE: 114
guccuucuau gcagcag                                               17

<210> SEQ ID NO 115
<211> LENGTH: 17
<212> TYPE: RNA
<213> ORGANISM: Homo sapiens

<400> SEQUENCE: 115
gggagccucu gcacagu                                               17

<210> SEQ ID NO 116
<211> LENGTH: 17
<212> TYPE: RNA
<213> ORGANISM: Homo sapiens

<400> SEQUENCE: 116
caguggcucc cugggga                                               17

<210> SEQ ID NO 117
<211> LENGTH: 17

```
<212> TYPE: RNA
<213> ORGANISM: Homo sapiens

<400> SEQUENCE: 117
ugugcacucc ggugguc                                                 17

<210> SEQ ID NO 118
<211> LENGTH: 17
<212> TYPE: RNA
<213> ORGANISM: Homo sapiens

<400> SEQUENCE: 118
ccggugguca ccuguac                                                 17

<210> SEQ ID NO 119
<211> LENGTH: 17
<212> TYPE: RNA
<213> ORGANISM: Homo sapiens

<400> SEQUENCE: 119
ucaccuguac ucccagc                                                 17

<210> SEQ ID NO 120
<211> LENGTH: 17
<212> TYPE: RNA
<213> ORGANISM: Homo sapiens

<400> SEQUENCE: 120
ccuguacucc cagcugc                                                 17

<210> SEQ ID NO 121
<211> LENGTH: 17
<212> TYPE: RNA
<213> ORGANISM: Homo sapiens

<400> SEQUENCE: 121
gcacugcuua cacgucu                                                 17

<210> SEQ ID NO 122
<211> LENGTH: 17
<212> TYPE: RNA
<213> ORGANISM: Homo sapiens

<400> SEQUENCE: 122
cacugcuuac acgucuu                                                 17

<210> SEQ ID NO 123
<211> LENGTH: 17
<212> TYPE: RNA
<213> ORGANISM: Homo sapiens

<400> SEQUENCE: 123
uuacacgucu uccuucg                                                 17

<210> SEQ ID NO 124
<211> LENGTH: 17
<212> TYPE: RNA
<213> ORGANISM: Homo sapiens

<400> SEQUENCE: 124
acacgucuuc cuucguc                                                 17

<210> SEQ ID NO 125
```

```
<211> LENGTH: 17
<212> TYPE: RNA
<213> ORGANISM: Homo sapiens

<400> SEQUENCE: 125
cacgucuucc uucgucu                                                    17

<210> SEQ ID NO 126
<211> LENGTH: 17
<212> TYPE: RNA
<213> ORGANISM: Homo sapiens

<400> SEQUENCE: 126
gucuuccuuc gucuuca                                                    17

<210> SEQ ID NO 127
<211> LENGTH: 17
<212> TYPE: RNA
<213> ORGANISM: Homo sapiens

<400> SEQUENCE: 127
ucuuccuucg ucuucac                                                    17

<210> SEQ ID NO 128
<211> LENGTH: 17
<212> TYPE: RNA
<213> ORGANISM: Homo sapiens

<400> SEQUENCE: 128
uccuucgucu ucaccua                                                    17

<210> SEQ ID NO 129
<211> LENGTH: 17
<212> TYPE: RNA
<213> ORGANISM: Homo sapiens

<400> SEQUENCE: 129
cuucgucuuc accuacc                                                    17

<210> SEQ ID NO 130
<211> LENGTH: 17
<212> TYPE: RNA
<213> ORGANISM: Homo sapiens

<400> SEQUENCE: 130
uucgucuuca ccuaccc                                                    17

<210> SEQ ID NO 131
<211> LENGTH: 17
<212> TYPE: RNA
<213> ORGANISM: Homo sapiens

<400> SEQUENCE: 131
cuucaccuac cccgagg                                                    17

<210> SEQ ID NO 132
<211> LENGTH: 17
<212> TYPE: RNA
<213> ORGANISM: Homo sapiens

<400> SEQUENCE: 132
ggcugacucc uucccca                                                    17
```

```
<210> SEQ ID NO 133
<211> LENGTH: 17
<212> TYPE: RNA
<213> ORGANISM: Homo sapiens

<400> SEQUENCE: 133
ugacuccuuc cccagcu                                                   17

<210> SEQ ID NO 134
<211> LENGTH: 17
<212> TYPE: RNA
<213> ORGANISM: Homo sapiens

<400> SEQUENCE: 134
gacuccuucc ccagcug                                                   17

<210> SEQ ID NO 135
<211> LENGTH: 17
<212> TYPE: RNA
<213> ORGANISM: Homo sapiens

<400> SEQUENCE: 135
augagccuuc cucugac                                                   17

<210> SEQ ID NO 136
<211> LENGTH: 17
<212> TYPE: RNA
<213> ORGANISM: Homo sapiens

<400> SEQUENCE: 136
ugagccuucc ucugacu                                                   17

<210> SEQ ID NO 137
<211> LENGTH: 17
<212> TYPE: RNA
<213> ORGANISM: Homo sapiens

<400> SEQUENCE: 137
gccuuccucu gacucgc                                                   17

<210> SEQ ID NO 138
<211> LENGTH: 17
<212> TYPE: RNA
<213> ORGANISM: Homo sapiens

<400> SEQUENCE: 138
cucugacucg cucagcu                                                   17

<210> SEQ ID NO 139
<211> LENGTH: 17
<212> TYPE: RNA
<213> ORGANISM: Homo sapiens

<400> SEQUENCE: 139
gacucgcuca gcucacc                                                   17

<210> SEQ ID NO 140
<211> LENGTH: 17
<212> TYPE: RNA
<213> ORGANISM: Homo sapiens

<400> SEQUENCE: 140
gcucagcuca cccacgc                                                   17
```

```
<210> SEQ ID NO 141
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 141
ucgcugcacu gaugangaaa ugcgguu                                     27

<210> SEQ ID NO 142
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 142
cuggguagcu gaugangaaa gcacggu                                     27

<210> SEQ ID NO 143
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 143
gagcugggcu gaugangaaa ggagcac                                     27

<210> SEQ ID NO 144
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 144
gugaagcacu gaugangaaa gcugggu                                     27

<210> SEQ ID NO 145
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 145
gcgcugugcu gaugangaaa gcagagc                                     27

<210> SEQ ID NO 146
<211> LENGTH: 27
<212> TYPE: RNA
```

<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 146
ggcgcugucu gaugangaaa agcagag                                              27

<210> SEQ ID NO 147
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 147
ggggcggacu gaugangaaa caggugg                                              27

<210> SEQ ID NO 148
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 148
gaggggcgcu gaugangaaa gacaggu                                              27

<210> SEQ ID NO 149
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 149
gaggggcccu gaugangaaa ggggcgg                                              27

<210> SEQ ID NO 150
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 150
agccgggccu gaugangaaa ggggccg                                              27

<210> SEQ ID NO 151
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:

<223> OTHER INFORMATION: The letter "n" represents stem II region of a
      HH ribozyme.

<400> SEQUENCE: 151
guuaggcacu gaugangaaa gccgggc                                             27

<210> SEQ ID NO 152
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 152
gguuaggccu gaugangaaa agccggg                                             27

<210> SEQ ID NO 153
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 153
guggcggucu gaugangaaa ggcaaag                                             27

<210> SEQ ID NO 154
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 154
agcccgagcu gaugangaaa caucauc                                             27

<210> SEQ ID NO 155
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 155
aagcccgacu gaugangaaa acaucau                                             27

<210> SEQ ID NO 156
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 156
cugcguugcu gaugangaaa gcccgag                                    27

<210> SEQ ID NO 157
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 157
ucugcguucu gaugangaaa agcccga                                    27

<210> SEQ ID NO 158
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 158
acgccucgcu gaugangaaa gucugcg                                    27

<210> SEQ ID NO 159
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 159
agcgggagcu gaugangaaa ugacgcc                                    27

<210> SEQ ID NO 160
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 160
ugcagcggcu gaugangaaa ggaugac                                    27

<210> SEQ ID NO 161
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 161
cggccgggcu gaugangaaa cgcgcug                                    27

<210> SEQ ID NO 162
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 162
agagaggccu gaugangaaa uccccgg                                          27

<210> SEQ ID NO 163
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 163
uaguaagacu gaugangaaa ggcuauc                                          27

<210> SEQ ID NO 164
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 164
gguaguaacu gaugangaaa gaggcua                                          27

<210> SEQ ID NO 165
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 165
gugguagucu gaugangaaa gagaggc                                          27

<210> SEQ ID NO 166
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 166
agugguagcu gaugangaaa agagagg                                          27

<210> SEQ ID NO 167
<211> LENGTH: 27
<212> TYPE: RNA
<213> ORGANISM: Artificial Sequence

```
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 167
gugaguggcu gaugangaaa guaagag                                              27

<210> SEQ ID NO 168
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 168 cugcggucu gaugangaaa gugguag                                               27

<210> SEQ ID NO 169
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 169
uggagaagcu gaugangaaa gucugcg                                              27

<210> SEQ ID NO 170
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 170
ugcuggagcu gaugangaaa ggagucu                                              27

<210> SEQ ID NO 171
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 171
augcuggacu gaugangaaa aggaguc                                              27

<210> SEQ ID NO 172
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
```

HH ribozyme.

<400> SEQUENCE: 172
ccaugcugcu gaugangaaa gaaggag                                                27

<210> SEQ ID NO 173
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
        HH ribozyme.

<400> SEQUENCE: 173
ugacaggccu gaugangaaa gcccaug                                                27

<210> SEQ ID NO 174
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
        HH ribozyme.

<400> SEQUENCE: 174
ugcgcguucu gaugangaaa caggcga                                                27

<210> SEQ ID NO 175
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
        HH ribozyme.

<400> SEQUENCE: 175
ccgugcagcu gaugangaaa guccugc                                                27

<210> SEQ ID NO 176
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
        HH ribozyme.

<400> SEQUENCE: 176
uccgugcacu gaugangaaa aguccug                                                27

<210> SEQ ID NO 177
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
        HH ribozyme.

<400> SEQUENCE: 177
gcacuggacu gaugangaaa cggccag					27

<210> SEQ ID NO 178
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 178
uggcacugcu gaugangaaa gacggcc					27

<210> SEQ ID NO 179
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 179
ugggaaugcu gaugangaaa guuggca					27

<210> SEQ ID NO 180
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 180
gugggaaucu gaugangaaa aguuggc					27

<210> SEQ ID NO 181
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 181
accgugggcu gaugangaaa ugaaguu					27

<210> SEQ ID NO 182
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 182
gaccguggcu gaugangaaa augaagu					27

<210> SEQ ID NO 183

<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 183
auggcagucu gaugangaaa ccguggg                                       27

<210> SEQ ID NO 184
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 184 cugucgacu gaugangaaa uggcagu                                        27

<210> SEQ ID NO 185
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 185
gacugguccu gaugangaaa gauggca                                       27

<210> SEQ ID NO 186
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 186
cagguccgcu gaugangaaa cuggucg                                       27

<210> SEQ ID NO 187
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 187
gaggagaccu gaugangaaa gggcggg                                       27

<210> SEQ ID NO 188
<211> LENGTH: 27
<212> TYPE: RNA
<213> ORGANISM: Artificial Sequence
<220> FEATURE:

<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 188
acagaggacu gaugangaaa cgagggc                                    27

<210> SEQ ID NO 189
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 189
ccacagagcu gaugangaaa gacgagg                                    27

<210> SEQ ID NO 190
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 190
gggccacacu gaugangaaa ggagacg                                    27

<210> SEQ ID NO 191
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 191
uggucugccu gaugangaaa ugggggcc                                   27

<210> SEQ ID NO 192
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 192
gaaagggucu gaugangaaa ggggcuc                                    27

<210> SEQ ID NO 193
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

```
<400> SEQUENCE: 193
gacuccgacu gaugangaaa gggugag                                27

<210> SEQ ID NO 194
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 194
ggacuccgcu gaugangaaa aggguga                                27

<210> SEQ ID NO 195
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 195
gggacucccu gaugangaaa aagggug                                27

<210> SEQ ID NO 196
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 196
ggggcgggcu gaugangaaa cuccgaa                                27

<210> SEQ ID NO 197
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 197
ccccagcgcu gaugangaaa gggggcg                                27

<210> SEQ ID NO 198
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 198
ccuggagucu gaugangaaa gccccag                                27
```

<210> SEQ ID NO 199
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 199
cccuggagcu gaugangaaa agcccca                                           27

<210> SEQ ID NO 200
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 200
cagcccugcu gaugangaaa guaagcc                                           27

<210> SEQ ID NO 201
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 201
gucuucaccu gaugangaaa cgccagc                                           27

<210> SEQ ID NO 202
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 202
cuccugcccu gaugangaaa ugcucug                                           27

<210> SEQ ID NO 203
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 203
cuggagaucu gaugangaaa cuguucc                                           27

<210> SEQ ID NO 204
<211> LENGTH: 27

```
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 204
ucuggagacu gaugangaaa acuguuc                                         27

<210> SEQ ID NO 205
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 205
cuucuggacu gaugangaaa uaacugu                                         27

<210> SEQ ID NO 206
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 206
uucuucugcu gaugangaaa gauaacu                                         27

<210> SEQ ID NO 207
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 207
ucccuucgcu gaugangaaa uucuccu                                         27

<210> SEQ ID NO 208
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 208
agccaucucu gaugangaaa uuccuuu                                         27

<210> SEQ ID NO 209
<211> LENGTH: 27
<212> TYPE: RNA
<213> ORGANISM: Artificial Sequence
<220> FEATURE:
<223> OTHER INFORMATION: Synthesized Hammerhead Ribozyme
```

<220> FEATURE:
<223> OTHER INFORMATION: The letter "n" represents stem II region of a
     HH ribozyme.

<400> SEQUENCE: 209
uuggagugcu gaugangaaa ucaguca                                              27

<210> SEQ ID NO 210
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
     HH ribozyme.

<400> SEQUENCE: 210
uccgcuugcu gaugangaaa guguauc                                              27

<210> SEQ ID NO 211
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
     HH ribozyme.

<400> SEQUENCE: 211
ucaucuuccu gaugangaaa guugguc                                              27

<210> SEQ ID NO 212
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
     HH ribozyme.

<400> SEQUENCE: 212
gcaaagcacu gaugangaaa cuucuca                                              27

<210> SEQ ID NO 213
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
     HH ribozyme.

<400> SEQUENCE: 213
ggucugcacu gaugangaaa gcagacu                                              27

<210> SEQ ID NO 214
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
     HH ribozyme.

```
<400> SEQUENCE: 214
cggucugccu gaugangaaa agcagac                                     27

<210> SEQ ID NO 215
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 215
agguuggccu gaugangaaa ucucggu                                     27

<210> SEQ ID NO 216
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 216
augaacuccu gaugangaaa guuuuuc                                     27

<210> SEQ ID NO 217
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 217
ccaggaugcu gaugangaaa cucuagu                                     27

<210> SEQ ID NO 218
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 218
gccaggaucu gaugangaaa acucuag                                     27

<210> SEQ ID NO 219
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 219
gcugccagcu gaugangaaa ugaacuc                                     27
```

<210> SEQ ID NO 220
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 220
aggucggucu gaugangaaa gcugcca                                              27

<210> SEQ ID NO 221
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 221
ucaucaggcu gaugangaaa ucuugca                                              27

<210> SEQ ID NO 222
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 222
cuucugggcu gaugangaaa gcccagg                                              27

<210> SEQ ID NO 223
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 223
ucuucuggcu gaugangaaa agcccag                                              27

<210> SEQ ID NO 224
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 224
aagccacacu gaugangaaa caucucu                                              27

<210> SEQ ID NO 225
<211> LENGTH: 27
<212> TYPE: RNA

<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
    HH ribozyme.

<400> SEQUENCE: 225
aucaagggcu gaugangaaa gccacag                                                27

<210> SEQ ID NO 226
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
    HH ribozyme.

<400> SEQUENCE: 226
gaucaaggcu gaugangaaa agccaca                                                27

<210> SEQ ID NO 227
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
    HH ribozyme.

<400> SEQUENCE: 227
gucagauccu gaugangaaa gggaagc                                                27

<210> SEQ ID NO 228
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
    HH ribozyme.

<400> SEQUENCE: 228
cccagucacu gaugangaaa ucaggg                                                 27

<210> SEQ ID NO 229
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
    HH ribozyme.

<400> SEQUENCE: 229 ggggguggccu gaugangaaa ccucugg                                               27

<210> SEQ ID NO 230
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:

<223> OTHER INFORMATION: The letter "n" represents stem II region of a
      HH ribozyme.

<400> SEQUENCE: 230
ccuccucacu gaugangaaa cuccggg                                              27

<210> SEQ ID NO 231
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 231
gcagggugcu gaugangaaa ggccucc                                              27

<210> SEQ ID NO 232
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 232
ggcagggucu gaugangaaa aggccuc                                              27

<210> SEQ ID NO 233
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 233
auugaggacu gaugangaaa ggcaggg                                              27

<210> SEQ ID NO 234
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 234
ucauugagcu gaugangaaa gaggcag                                              27

<210> SEQ ID NO 235
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 235
gggucauucu gaugangaaa ggagagg                                        27

<210> SEQ ID NO 236
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 236
guuccacucu gaugangaaa gggcuug                                        27

<210> SEQ ID NO 237
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 237
augcucuucu gaugangaaa cagguuc                                        27

<210> SEQ ID NO 238
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 238
augcugcucu gaugangaaa ugcucuu                                        27

<210> SEQ ID NO 239
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 239
agucaucacu gaugangaaa gggcucg                                        27

<210> SEQ ID NO 240
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 240
aagucauccu gaugangaaa agggcuc                                        27

```
<210> SEQ ID NO 241
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 241
ggaacaggcu gaugangaaa gucauca                                              27

<210> SEQ ID NO 242
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 242
gggaacagcu gaugangaaa agucauc                                              27

<210> SEQ ID NO 243
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 243
augcugggcu gaugangaaa caggaag                                              27

<210> SEQ ID NO 244
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 244
gaugcuggcu gaugangaaa acaggaa                                              27

<210> SEQ ID NO 245
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 245
gccuggaucu gaugangaaa ugcuggg                                              27

<210> SEQ ID NO 246
<211> LENGTH: 27
<212> TYPE: RNA
<213> ORGANISM: Artificial Sequence
```

```
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 246
ugggccugcu gaugangaaa ugaugcu                                       27

<210> SEQ ID NO 247
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 247
cugucucacu gaugangaaa gccacug                                       27

<210> SEQ ID NO 248
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 248
cuggcacgcu gaugangaaa gcgggcu                                       27

<210> SEQ ID NO 249
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 249
gacccagacu gaugangaaa gguccau                                       27

<210> SEQ ID NO 250
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 250
aggacccacu gaugangaaa uaggucc                                       27

<210> SEQ ID NO 251
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
```

HH ribozyme.

<400> SEQUENCE: 251
cauagaagcu gaugangaaa cccagau        27

<210> SEQ ID NO 252
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 252
cugcauagcu gaugangaaa ggaccca        27

<210> SEQ ID NO 253
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 253
gcugcauacu gaugangaaa aggaccc        27

<210> SEQ ID NO 254
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 254
cugcugcacu gaugangaaa gaaggac        27

<210> SEQ ID NO 255
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 255
acugugcacu gaugangaaa ggcuccc        27

<210> SEQ ID NO 256
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 256
uccccaggcu gaugangaaa gccacug                               27

<210> SEQ ID NO 257
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 257
gaccaccgcu gaugangaaa gugcaca                               27

<210> SEQ ID NO 258
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 258
guacaggucu gaugangaaa ccaccgg                               27

<210> SEQ ID NO 259
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 259
gcugggagcu gaugangaaa cagguga                               27

<210> SEQ ID NO 260
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 260
gcagcuggcu gaugangaaa guacagg                               27

<210> SEQ ID NO 261
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 261
agacgugucu gaugangaaa gcagugc                               27

<210> SEQ ID NO 262

<211> LENGTH: 27
    <212> TYPE: RNA
    <213> ORGANISM: Artificial Sequence
    <220> FEATURE:
    <223> OTHER INFORMATION: Synthesized Hammerhead Ribozyme
    <220> FEATURE:
    <223> OTHER INFORMATION: The letter "n" represents stem II region of a
          HH ribozyme.

<400> SEQUENCE: 262
aagacgugcu gaugangaaa agcagug                                              27

<210> SEQ ID NO 263
    <211> LENGTH: 27
    <212> TYPE: RNA
    <213> ORGANISM: Artificial Sequence
    <220> FEATURE:
    <223> OTHER INFORMATION: Synthesized Hammerhead Ribozyme
    <220> FEATURE:
    <223> OTHER INFORMATION: The letter "n" represents stem II region of a
          HH ribozyme.

<400> SEQUENCE: 263
cgaaggaacu gaugangaaa cguguaa                                              27

<210> SEQ ID NO 264
    <211> LENGTH: 27
    <212> TYPE: RNA
    <213> ORGANISM: Artificial Sequence
    <220> FEATURE:
    <223> OTHER INFORMATION: Synthesized Hammerhead Ribozyme
    <220> FEATURE:
    <223> OTHER INFORMATION: The letter "n" represents stem II region of a
          HH ribozyme.

<400> SEQUENCE: 264
gacgaaggcu gaugangaaa gacgugu                                              27

<210> SEQ ID NO 265
    <211> LENGTH: 27
    <212> TYPE: RNA
    <213> ORGANISM: Artificial Sequence
    <220> FEATURE:
    <223> OTHER INFORMATION: Synthesized Hammerhead Ribozyme
    <220> FEATURE:
    <223> OTHER INFORMATION: The letter "n" represents stem II region of a
          HH ribozyme.

<400> SEQUENCE: 265
agacgaagcu gaugangaaa agacgug                                              27

<210> SEQ ID NO 266
    <211> LENGTH: 27
    <212> TYPE: RNA
    <213> ORGANISM: Artificial Sequence
    <220> FEATURE:
    <223> OTHER INFORMATION: Synthesized Hammerhead Ribozyme
    <220> FEATURE:
    <223> OTHER INFORMATION: The letter "n" represents stem II region of a
          HH ribozyme.

<400> SEQUENCE: 266
ugaagacgcu gaugangaaa ggaagac                                              27

<210> SEQ ID NO 267
    <211> LENGTH: 27
    <212> TYPE: RNA
    <213> ORGANISM: Artificial Sequence
    <220> FEATURE:

<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 267
gugaagaccu gaugangaaa aggaaga                                        27

<210> SEQ ID NO 268
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 268
uaggugaacu gaugangaaa cgaagga                                        27

<210> SEQ ID NO 269
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 269
gguaggugcu gaugangaaa gacgaag                                        27

<210> SEQ ID NO 270
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 270
ggguaggucu gaugangaaa agacgaa                                        27

<210> SEQ ID NO 271
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 271
ccucggggcu gaugangaaa ggugaag                                        27

<210> SEQ ID NO 272
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 272 ugggaagcu gaugangaaa gucagcc                                27

<210> SEQ ID NO 273
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 273
agcuggggcu gaugangaaa ggaguca                               27

<210> SEQ ID NO 274
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 274
cagcugggcu gaugangaaa aggaguc                               27

<210> SEQ ID NO 275
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 275
gucagaggcu gaugangaaa ggcucau                               27

<210> SEQ ID NO 276
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 276
agucagagcu gaugangaaa aggcuca                               27

<210> SEQ ID NO 277
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 277
gcgagucacu gaugangaaa ggaaggc                               27

<210> SEQ ID NO 278
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 278
agcugagccu gaugangaaa gucagag                                              27

<210> SEQ ID NO 279
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 279
ggugagcucu gaugangaaa gcgaguc                                              27

<210> SEQ ID NO 280
<211> LENGTH: 27
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" represents stem II region of a
      HH ribozyme.

<400> SEQUENCE: 280
gcgugggucu gaugangaaa gcugagc                                              27

<210> SEQ ID NO 281
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 281
cgccgcagaa gccgaccaga gaaacacacg uugugguaca uuaccugua                      50

<210> SEQ ID NO 282
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 282
aagcagagaa ggguaccaga gaaacacacg uugugguaca uuaccugua                      50

<210> SEQ ID NO 283
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 283
cugugaagaa gagcaccaga gaaacacacg uugugguaca uuaccggua        50

<210> SEQ ID NO 284
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 284
ggcggaagaa ggugaccaga gaaacacacg uugugguaca uuaccggua        50

<210> SEQ ID NO 285
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 285
ccgaggagaa gagaaccaga gaaacacacg uugugguaca uuaccggua        50

<210> SEQ ID NO 286
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 286
gcgaggagaa gaggaccaga gaaacacacg uugugguaca uuaccggua        50

<210> SEQ ID NO 287
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 287
aggcaaagaa gggcaccaga gaaacacacg uugugguaca uuaccggua        50

<210> SEQ ID NO 288
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 288
cucguaagaa gcguaccaga gaaacacacg uugugguaca uuaccggua        50

<210> SEQ ID NO 289
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 289
ugcugcagaa ggagaccaga gaaacacacg uugugguaca uuaccggua        50

<210> SEQ ID NO 290
<211> LENGTH: 50
<212> TYPE: RNA

<213> ORGANISM: Artificial Sequence
<220> FEATURE:
<223> OTHER INFORMATION: Synthesized Hairpin Ribozyme

<400> SEQUENCE: 290
auccccagaa ggggaccaga gaaacacacg uugugguaca uuaccggua          50

<210> SEQ ID NO 291
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 291
gaaggaagaa gcggaccaga gaaacacacg uugugguaca uuaccggua          50

<210> SEQ ID NO 292
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 292
ggccagagaa gugcaccaga gaaacacacg uugugguaca uuaccggua          50

<210> SEQ ID NO 293
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 293
acuggaagaa gccaaccaga gaaacacacg uugugguaca uuaccggua          50

<210> SEQ ID NO 294
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 294
gguccgagaa ggucaccaga gaaacacacg uugugguaca uuaccggua          50

<210> SEQ ID NO 295
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 295
cugcagagaa ggacaccaga gaaacacacg uugugguaca uuaccggua          50

<210> SEQ ID NO 296
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 296
agggcgagaa gcacaccaga gaaacacacg uugugguaca uuaccggua          50

<210> SEQ ID NO 297
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 297
gacgagagaa ggcuaccaga gaaacacacg uugugguaca uuaccuggua          50

<210> SEQ ID NO 298
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 298
gcucugagaa gcgaaccaga gaaacacacg uugugguaca uuaccuggua          50

<210> SEQ ID NO 299
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 299
ggagggagaa gggaaccaga gaaacacacg uugugguaca uuaccuggua          50

<210> SEQ ID NO 300
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 300
agccccagaa gaggaccaga gaaacacacg uugugguaca uuaccuggua          50

<210> SEQ ID NO 301
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 301
guaucaagaa gcucaccaga gaaacacacg uugugguaca uuaccuggua          50

<210> SEQ ID NO 302
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 302
uaguugagaa gucuaccaga gaaacacacg uugugguaca uuaccuggua          50

<210> SEQ ID NO 303
<211> LENGTH: 50
<212> TYPE: RNA
<213> ORGANISM: Artificial Sequence
<220> FEATURE:

<223> OTHER INFORMATION: Synthesized Hairpin Ribozyme

<400> SEQUENCE: 303
cugcaaagaa gacuaccaga gaaacacacg uugugguaca uuaccggua          50

<210> SEQ ID NO 304
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 304
aucucgagaa gcaaaccaga gaaacacacg uugugguaca uuaccggua          50

<210> SEQ ID NO 305
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 305
uccuucagaa gguuaccaga gaaacacacg uugugguaca uuaccggua          50

<210> SEQ ID NO 306
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 306
ucggugagaa gccaaccaga gaaacacacg uugugguaca uuaccggua          50

<210> SEQ ID NO 307
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 307
aggcagagaa gugaaccaga gaaacacacg uugugguaca uuaccggua          50

<210> SEQ ID NO 308
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 308
cuugcaagaa ggucaccaga gaaacacacg uugugguaca uuaccggua          50

<210> SEQ ID NO 309
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 309
caggucagaa gggaaccaga gaaacacacg uugugguaca uuaccggua          50

<210> SEQ ID NO 310
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 310
cccccaagaa gaucaccaga gaaacacacg uugugguaca uuaccuggua          50

<210> SEQ ID NO 311
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 311
aggagaagaa ggguaccaga gaaacacacg uugugguaca uuaccuggua          50

<210> SEQ ID NO 312
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 312
gcugggagaa ggaaaccaga gaaacacacg uugugguaca uuaccuggua          50

<210> SEQ ID NO 313
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 313
ggagcgagaa gucuaccaga gaaacacacg uugugguaca uuaccuggua          50

<210> SEQ ID NO 314
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 314
gcacggagaa ggcuaccaga gaaacacacg uugugguaca uuaccuggua          50

<210> SEQ ID NO 315
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 315
cucccaagaa gcugaccaga gaaacacacg uugugguaca uuaccuggua          50

<210> SEQ ID NO 316
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 316
cagugcagaa gggaaccaga gaaacacacg uugugguaca uuaccuggua         50

<210> SEQ ID NO 317
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 317
cguguaagaa gugcaccaga gaaacacacg uugugguaca uuaccuggua         50

<210> SEQ ID NO 318
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 318
gaaggaagaa gccuaccaga gaaacacacg uugugguaca uuaccuggua         50

<210> SEQ ID NO 319
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 319
cugcacagaa ggggaccaga gaaacacacg uugugguaca uuaccuggua         50

<210> SEQ ID NO 320
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 320
gugggcagaa gcacaccaga gaaacacacg uugugguaca uuaccuggua         50

<210> SEQ ID NO 321
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 321
gcggugagaa gcugaccaga gaaacacacg uugugguaca uuaccuggua         50

<210> SEQ ID NO 322
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 322
gagcgaagaa gaggaccaga gaaacacacg uugugguaca uuaccuggua         50

<210> SEQ ID NO 323
<211> LENGTH: 50

-continued

```
<212> TYPE: RNA
<213> ORGANISM: Artificial Sequence
<220> FEATURE:
<223> OTHER INFORMATION: Synthesized Hairpin Ribozyme

<400> SEQUENCE: 323
ugggugagaa gagcaccaga gaaacacacg uugugguaca uuaccugua          50

<210> SEQ ID NO 324
<211> LENGTH: 50
<212> TYPE: RNA
<213> ORGANISM: Artificial Sequence
<220> FEATURE:
<223> OTHER INFORMATION: Synthesized Hairpin Ribozyme

<400> SEQUENCE: 324
agggccagaa gcguaccaga gaaacacacg uugugguaca uuaccugua          50

<210> SEQ ID NO 325
<211> LENGTH: 14
<212> TYPE: RNA
<213> ORGANISM: Homo sapiens

<400> SEQUENCE: 325
cggcggccgc ggcg                                                14

<210> SEQ ID NO 326
<211> LENGTH: 14
<212> TYPE: RNA
<213> ORGANISM: Homo sapiens

<400> SEQUENCE: 326
acccagcucu gcuu                                                14

<210> SEQ ID NO 327
<211> LENGTH: 14
<212> TYPE: RNA
<213> ORGANISM: Homo sapiens

<400> SEQUENCE: 327
gcucugcuuc acag                                                14

<210> SEQ ID NO 328
<211> LENGTH: 14
<212> TYPE: RNA
<213> ORGANISM: Homo sapiens

<400> SEQUENCE: 328
caccugucuc cgcc                                                14

<210> SEQ ID NO 329
<211> LENGTH: 14
<212> TYPE: RNA
<213> ORGANISM: Homo sapiens

<400> SEQUENCE: 329
ucuccgcccc ucgg                                                14

<210> SEQ ID NO 330
<211> LENGTH: 14
<212> TYPE: RNA
<213> ORGANISM: Homo sapiens

<400> SEQUENCE: 330
```
ccucggcccc ucgc                                          14

<210> SEQ ID NO 331
<211> LENGTH: 14
<212> TYPE: RNA
<213> ORGANISM: Homo sapiens

<400> SEQUENCE: 331
gcccggcuuu gccu                                          14

<210> SEQ ID NO 332
<211> LENGTH: 14
<212> TYPE: RNA
<213> ORGANISM: Homo sapiens

<400> SEQUENCE: 332
acgcagacua cgag                                          14

<210> SEQ ID NO 333
<211> LENGTH: 14
<212> TYPE: RNA
<213> ORGANISM: Homo sapiens

<400> SEQUENCE: 333 cuccccgcugc agca                                         14

<210> SEQ ID NO 334
<211> LENGTH: 14
<212> TYPE: RNA
<213> ORGANISM: Homo sapiens

<400> SEQUENCE: 334
ccccggccgg ggau                                          14

<210> SEQ ID NO 335
<211> LENGTH: 14
<212> TYPE: RNA
<213> ORGANISM: Homo sapiens

<400> SEQUENCE: 335
ccgcagacuc cuuc                                          14

<210> SEQ ID NO 336
<211> LENGTH: 14
<212> TYPE: RNA
<213> ORGANISM: Homo sapiens

<400> SEQUENCE: 336
gcacggaccu ggcc                                          14

<210> SEQ ID NO 337
<211> LENGTH: 14
<212> TYPE: RNA
<213> ORGANISM: Homo sapiens

<400> SEQUENCE: 337
uggccgucuc cagu                                          14

<210> SEQ ID NO 338
<211> LENGTH: 14
<212> TYPE: RNA
<213> ORGANISM: Homo sapiens

<400> SEQUENCE: 338

```
gaccaguccg gacc                                                    14

<210> SEQ ID NO 339
<211> LENGTH: 14
<212> TYPE: RNA
<213> ORGANISM: Homo sapiens

<400> SEQUENCE: 339
guccggaccu gcag                                                    14

<210> SEQ ID NO 340
<211> LENGTH: 14
<212> TYPE: RNA
<213> ORGANISM: Homo sapiens

<400> SEQUENCE: 340
gugcagcccg cccu                                                    14

<210> SEQ ID NO 341
<211> LENGTH: 14
<212> TYPE: RNA
<213> ORGANISM: Homo sapiens

<400> SEQUENCE: 341
agcccgcccu cguc                                                    14

<210> SEQ ID NO 342
<211> LENGTH: 14
<212> TYPE: RNA
<213> ORGANISM: Homo sapiens

<400> SEQUENCE: 342
ucgcagacca gagc                                                    14

<210> SEQ ID NO 343
<211> LENGTH: 14
<212> TYPE: RNA
<213> ORGANISM: Homo sapiens

<400> SEQUENCE: 343
uccccgcccc cucc                                                    14

<210> SEQ ID NO 344
<211> LENGTH: 14
<212> TYPE: RNA
<213> ORGANISM: Homo sapiens

<400> SEQUENCE: 344
ccuccgcugg ggcu                                                    14

<210> SEQ ID NO 345
<211> LENGTH: 14
<212> TYPE: RNA
<213> ORGANISM: Homo sapiens

<400> SEQUENCE: 345
gagcugacug auac                                                    14

<210> SEQ ID NO 346
<211> LENGTH: 14
<212> TYPE: RNA
<213> ORGANISM: Homo sapiens
```

```
<400> SEQUENCE: 346
agacagacca acua                                                    14

<210> SEQ ID NO 347
<211> LENGTH: 14
<212> TYPE: RNA
<213> ORGANISM: Homo sapiens

<400> SEQUENCE: 347
agucugcuuu gcag                                                    14

<210> SEQ ID NO 348
<211> LENGTH: 14
<212> TYPE: RNA
<213> ORGANISM: Homo sapiens

<400> SEQUENCE: 348
uugcagaccg agau                                                    14

<210> SEQ ID NO 349
<211> LENGTH: 14
<212> TYPE: RNA
<213> ORGANISM: Homo sapiens

<400> SEQUENCE: 349
aaccugcuga agga                                                    14

<210> SEQ ID NO 350
<211> LENGTH: 14
<212> TYPE: RNA
<213> ORGANISM: Homo sapiens

<400> SEQUENCE: 350
uggcagcuca ccga                                                    14

<210> SEQ ID NO 351
<211> LENGTH: 14
<212> TYPE: RNA
<213> ORGANISM: Homo sapiens

<400> SEQUENCE: 351
ucaccgaccu gccu                                                    14

<210> SEQ ID NO 352
<211> LENGTH: 14
<212> TYPE: RNA
<213> ORGANISM: Homo sapiens

<400> SEQUENCE: 352
gaccugccug caag                                                    14

<210> SEQ ID NO 353
<211> LENGTH: 14
<212> TYPE: RNA
<213> ORGANISM: Homo sapiens

<400> SEQUENCE: 353
ucccugauga ccug                                                    14

<210> SEQ ID NO 354
<211> LENGTH: 14
<212> TYPE: RNA
<213> ORGANISM: Homo sapiens
```

<400> SEQUENCE: 354
gaucugacug gggg                                                      14

<210> SEQ ID NO 355
<211> LENGTH: 14
<212> TYPE: RNA
<213> ORGANISM: Homo sapiens

<400> SEQUENCE: 355
acccugccuc uccu                                                      14

<210> SEQ ID NO 356
<211> LENGTH: 14
<212> TYPE: RNA
<213> ORGANISM: Homo sapiens

<400> SEQUENCE: 356
uuccuguucc cagc                                                      14

<210> SEQ ID NO 357
<211> LENGTH: 14
<212> TYPE: RNA
<213> ORGANISM: Homo sapiens

<400> SEQUENCE: 357
agacagcccg cucc                                                      14

<210> SEQ ID NO 358
<211> LENGTH: 14
<212> TYPE: RNA
<213> ORGANISM: Homo sapiens

<400> SEQUENCE: 358
agcccgcucc gugc                                                      14

<210> SEQ ID NO 359
<211> LENGTH: 14
<212> TYPE: RNA
<213> ORGANISM: Homo sapiens

<400> SEQUENCE: 359
cagcagacug ggag                                                      14

<210> SEQ ID NO 360
<211> LENGTH: 14
<212> TYPE: RNA
<213> ORGANISM: Homo sapiens

<400> SEQUENCE: 360
ucccagcugc acug                                                      14

<210> SEQ ID NO 361
<211> LENGTH: 14
<212> TYPE: RNA
<213> ORGANISM: Homo sapiens

<400> SEQUENCE: 361
gcacugcuua cacg                                                      14

<210> SEQ ID NO 362
<211> LENGTH: 14
<212> TYPE: RNA

```
<213> ORGANISM: Homo sapiens

<400> SEQUENCE: 362
aggcugacuc cuuc                                                          14

<210> SEQ ID NO 363
<211> LENGTH: 14
<212> TYPE: RNA
<213> ORGANISM: Homo sapiens

<400> SEQUENCE: 363
ccccagcugu gcag                                                          14

<210> SEQ ID NO 364
<211> LENGTH: 14
<212> TYPE: RNA
<213> ORGANISM: Homo sapiens

<400> SEQUENCE: 364
gugcagcugc ccac                                                          14

<210> SEQ ID NO 365
<211> LENGTH: 14
<212> TYPE: RNA
<213> ORGANISM: Homo sapiens

<400> SEQUENCE: 365
cagcugccca ccgc                                                          14

<210> SEQ ID NO 366
<211> LENGTH: 14
<212> TYPE: RNA
<213> ORGANISM: Homo sapiens

<400> SEQUENCE: 366
ccucugacuc gcuc                                                          14

<210> SEQ ID NO 367
<211> LENGTH: 14
<212> TYPE: RNA
<213> ORGANISM: Homo sapiens

<400> SEQUENCE: 367
gcucagcuca ccca                                                          14

<210> SEQ ID NO 368
<211> LENGTH: 14
<212> TYPE: RNA
<213> ORGANISM: Homo sapiens

<400> SEQUENCE: 368
acgcugcugg cccu                                                          14

<210> SEQ ID NO 369
<211> LENGTH: 11
<212> TYPE: RNA
<213> ORGANISM: Artificial Sequence
<220> FEATURE:
<223> OTHER INFORMATION: Synthesized Hammerhead Ribozyme Target
<220> FEATURE:
<223> OTHER INFORMATION: The letter "n" stands for any base;
      The letter "h" stands for a, c or t.

<400> SEQUENCE: 369
```
nnnnuhnnnn n                                                                      11

<210> SEQ ID NO 370
<211> LENGTH: 28
<212> TYPE: RNA
<213> ORGANISM: Artificial Sequence
<220> FEATURE:
<223> OTHER INFORMATION: Synthesized Hammerhead Ribozyme
<220> FEATURE:
<223> OTHER INFORMATION: The letter "n" stands for any base.

<400> SEQUENCE: 370
nnnnncugan gagnnnnnnc gaaannnn                                                    28

<210> SEQ ID NO 371
<211> LENGTH: 15
<212> TYPE: RNA
<213> ORGANISM: Artificial Sequence
<220> FEATURE:
<223> OTHER INFORMATION: Synthesized Hairpin Ribozyme Target
<220> FEATURE:
<223> OTHER INFORMATION: The letter "n" stands for any base;
      The letter "y" stands for c or t;
      The letter "h" stands for a, c or t.

<400> SEQUENCE: 371
nnnnnnnyng hynnn                                                                  15

<210> SEQ ID NO 372
<211> LENGTH: 47
<212> TYPE: RNA
<213> ORGANISM: Artificial Sequence
<220> FEATURE:
<223> OTHER INFORMATION: Synthesized Hairpin Ribozyme
<220> FEATURE:
<223> OTHER INFORMATION: The letter "n" stands for any base;
      The letter "h" stands for a, c or t.

<400> SEQUENCE: 372
nnnngaagnn nnnnnnnnna aahannnnnn nacauuacnn nnnnnnn                               47

<210> SEQ ID NO 373
<211> LENGTH: 49
<212> TYPE: RNA
<213> ORGANISM: Artificial Sequence
<220> FEATURE:
<223> OTHER INFORMATION: Synthesized Hepatitis Delta Virus (HDV)
      Ribozyme
<220> FEATURE:
<223> OTHER INFORMATION: The letter "n" stands for any base.

<400> SEQUENCE: 373
cuccaccucc ucgcggunnn nnnngggcua cuucgguagg cuaagggag                             49

<210> SEQ ID NO 374
<211> LENGTH: 176
<212> TYPE: RNA
<213> ORGANISM: Artificial Sequence
<220> FEATURE:
<223> OTHER INFORMATION: Synthesized Neurospora VS Ribozyme

<400> SEQUENCE: 374
gggaaagcuu gcgaagggcg ucgucgcccc gagcgguagu aagcagggaa cucaccucca               60
auuucaguac ugaaauuguc guagcaguug acuacuguua ugugauuggu agaggcuaag              120
ugacgguauu ggcguaaguc aguauugcag cacagcacaa gcccgcuugc gagaau                 176

-continued

```
<210> SEQ ID NO 375
<211> LENGTH: 37
<212> TYPE: RNA
<213> ORGANISM: Artificial Sequence
<220> FEATURE:
<223> OTHER INFORMATION: Synthesized Amino Hammerhead Ribozyme
<220> FEATURE:
<223> OTHER INFORMATION: The letter "n" stands for any base.
      The letter "h" stands for a, c or t.

<400> SEQUENCE: 375
nnnnnnncug augaggccga aaggccgaaa nnnnnnh                               37
```